US006604698B2

(12) United States Patent
Verhoff et al.

(10) Patent No.: US 6,604,698 B2
(45) Date of Patent: Aug. 12, 2003

(54) MEDIA MILLING

(75) Inventors: Frank H. Verhoff, Cincinnati, OH (US); Robert A. Snow, West Chester, PA (US); Gary W. Pace, Raleigh, NC (US)

(73) Assignee: SkyePharma Canada, Inc., Montreal (CA)

( * ) Notice: Subject to any disclaimer, the term of this patent is extended or adjusted under 35 U.S.C. 154(b) by 50 days.

(21) Appl. No.: 09/852,054

(22) Filed: May 10, 2001

(65) Prior Publication Data

US 2002/0003179 A1 Jan. 10, 2002

Related U.S. Application Data

(60) Provisional application No. 60/203,366, filed on May 10, 2000.

(51) Int. Cl.[7] .......................... B02C 17/16; B02C 19/12
(52) U.S. Cl. .......................................... 241/21; 214/184
(58) Field of Search ................................ 214/184, 172, 214/171, 30, 21, 18, 57, 62; 424/450

(56) References Cited

U.S. PATENT DOCUMENTS

| | | | | |
|---|---|---|---|---|
| 178,266 | A | * 6/1876 | Bruckner | 241/172 |
| 536,112 | A | * 3/1895 | Western | 241/171 |
| 2,041,287 | A | * 5/1936 | Frisch | 241/171 |
| 4,006,025 | A | 2/1977 | Swank et al. | |
| 4,294,916 | A | 10/1981 | Postle et al. | |
| 4,294,917 | A | 10/1981 | Postle et al. | |
| 4,880,634 | A | 11/1989 | Speiser | |
| 4,927,744 | A | 5/1990 | Henzel et al. | |
| 4,940,654 | A | 7/1990 | Diehl et al. | |

(List continued on next page.)

FOREIGN PATENT DOCUMENTS

| | | |
|---|---|---|
| DE | 12 91 607 B | 3/1969 |
| DE | 3837412 | 5/1990 |
| EP | 498482 | 8/1992 |
| GB | 1570362 | 7/1980 |
| WO | WO 9714407 | 4/1997 |
| WO | WO 9939700 | 8/1999 |

OTHER PUBLICATIONS

Pace et al., "Novel Injectable Formulations of Insolube Drugs", *Pharmaceutical Technology*, vol. 23, No. 3, (Mar. 1999), pp. 116–134.

Primary Examiner—Mark Rosenbaum
(74) Attorney, Agent, or Firm—Edwards & Angell, LLP

(57) ABSTRACT

This invention describes a process for preparing a dispersion of solid particles of a milled substrate in a fluid carrier comprising the steps of (a) providing a plurality of large size milling media to the milling chamber of a media mill and forming a depth filter therefrom on an exit screen or separator in the milling chamber; (b) adding to said milling chamber a plurality of small size milling media optionally containing additional large size milling media, a conglomerate of a solid substance comprising a substrate to be milled and optionally one or more than one surface active substance, and a fluid carrier; (c) milling said conglomerate in said milling chamber to produce very small milled substrate product particles; and (d) separating said milled substrate particles suspended in said fluid carrier from the media through said depth filter; wherein the exit screen comprises openings of size $S_0$; the large size media have a size distribution $S_1$ of which all are larger than $S_0$; the small size media have a size distribution $S_2$ which are smaller than $S_0$; the very small milled substrate particles have a size distribution $S_3$ and are smaller than all of the small media; and the large size media and the small size media are essentially retained in the milling chamber.

31 Claims, 4 Drawing Sheets

U.S. PATENT DOCUMENTS

| | | |
|---|---|---|
| 4,950,586 A | 8/1990 | Diehl et al. |
| 5,091,187 A | 2/1992 | Haynes |
| 5,091,188 A | 2/1992 | Haynes |
| 5,145,684 A | 9/1992 | Liversidge et al. |
| 5,257,742 A | 11/1993 | Yashima et al. |
| 5,302,401 A | 4/1994 | Liversidge et al. |
| 5,336,507 A | 8/1994 | Na et al. |
| 5,470,583 A | 11/1995 | Na et al. |
| 5,478,705 A | 12/1995 | Czekai et al. |
| 5,500,331 A | 3/1996 | Czekai et al. |
| 5,513,803 A | 5/1996 | Czekai et al. |
| 5,518,187 A | 5/1996 | Bruno et al. |
| 5,534,270 A | 7/1996 | De Castro |
| 5,657,931 A | 8/1997 | Nair et al. |
| 5,662,279 A | 9/1997 | Czekai et al. |
| 5,700,471 A | 12/1997 | End et al. |
| 5,704,556 A | 1/1998 | McLaughlin |
| 5,718,388 A | 2/1998 | Czekai et al. |
| 5,862,999 A | 1/1999 | Czekai et al. |
| 5,902,711 A | 5/1999 | Smith et al. |
| 5,922,355 A | 7/1999 | Parikh et al. |

* cited by examiner

MEDIA MILLING

This application claims the benefit of Provisional Application No. 60/203,366 filed May 10, 2000.

FIELD OF THE INVENTION

This invention relates to media milling and in particular to media milling using two size distributions of milling media to obtain small particles of a solid material wherein the media are retained in the milling chamber of the media mill and the small particles are separated from the milling media.

BACKGROUND OF THE INVENTION

Size reduction of crystalline and amorphous solids by mechanical means using dry or wet milling techniques such as jet milling, ball milling, media milling, or homogenization is now widely used in a variety of industries. Diverse industrial applications include the production of paints; pigments; photographic materials; cosmetics; chemicals; metal powders useful as catalysts and supports; stationary phase particles useful in analytical and preparative chromatographic separations of chemical compounds and mixtures such as those encountered in forensic science, food, cosmetics, chemical, and pharmaceutical studies; powdered toners, both black and colored, useful in xerographic and printing applications including laser printing; and small particles of solid pharmaceutical agents including water-soluble, water-insoluble, and poorly water-soluble therapeutic and diagnostic imaging agents, medicinally active agents, medicaments, plant and herbal extracts, drugs, pro-drugs, drug formulations, diagnostic imaging agents, and the like. In pharmaceutical applications it is often desirable to prepare very small particles of an essentially water-insoluble or poorly water solid because the rate of dissolution of a particle and often the bioavailability of an essentially water-insoluble or poorly water-soluble drug can increase with increasing surface area, i.e., decreasing particle size.

Examples of mills used to accomplish particle size reduction include colloid mills, swinging mills, ball mills, media mills, attritor mills, jet mills, vibratory mills, and high pressure homogenizers. Size reduction methods are described, e.g., in U.S. Pat. Nos. 4,006,025, 4,294,916, 4,294,917, 4,940,654, 4,950,586 and 4,927,744, and UK 1,570,362.

In a communition or milling process, repeated collisions of milling media with a solid material being milled, i.e., the milled substrate, result in repeated fracture of the substrate and concomitant substrate particle size reduction. When a media milling process is used to reduce the size of particles of a substrate, the process is usually carried out in a mill comprising a milling chamber containing milling media, a solid material or substrate which is to be milled, and a liquid or gaseous fluid carrier in which the media and substrate are suspended. The contents of the milling chamber are stirred or agitated with an agitator which transfers energy to the milling media. The accelerated media collide with the substrate in energetic collisions that can crush, chip, fracture or otherwise reduce the size of the solid substrate material and lead to an overall reduction in substrate particle size and an overall reduction in substrate average or mean particle size distribution.

Milling media are generally selected from a variety of dense and hard materials, such as sand, steel, silicon carbide, ceramics, zirconium silicate, zirconium and yttrium oxide, glass, alumina, titanium, and certain polymers such as crosslinked polystyrene and methyl methacrylate. Polymeric media are sometimes preferable to conventional inorganic media because they do not degrade to deposit metal oxides and soluble salts in the milled substrate and pH fluctuations and chemical changes can be minimized during milling. Such changes may impair dispersion stability, hydrolyze certain solids, and alter milling performance. Media geometries may vary depending on the application, although spherical or cylindrical beads are most commonly used.

Milling media can be of various sizes and size distributions that include large milling media particles and smaller milling media particles. The size distribution of the milling media can be narrow in which case the media are substantially uniform or nearly uniform in size. Alternatively, more than one narrow size distribution of media can be used. If two substantially different media sizes are used wherein substantially all of the media can be classified as being of either one or the other size, then the size distribution of the milling media can be described as being bimodal. Bimodal size distributions of milling media are often used in a milling chamber containing a separator having openings smaller than the smallest size of media used. Such a separator or screen will not allow any size of media used in a bimodal or broad distribution of media sizes to pass out of the milling chamber. Alternatively, the milling media can be sufficiently small that substantially all of the milling media can pass through the openings in the separator or screen and thus pass out of the milling chamber. Alternatively, the size of the openings in the milling separator can be small enough to prohibit passage of one size distribution of media (i.e., a larger size) but permit the passage of another size distribution of media (i.e., a smaller size distribution of milling media).

Mills useful for reducing the particle size of a solid substrate can operate in a batchwise mode or in a continuous or semi-continuous mode. Mills operating in a continuous mode often incorporate a means such as a separator or screen for retaining milling media together with relatively large particles of the solid substrate being milled in the milling zone or milling chamber of the mill while allowing smaller particles of the substrate being milled, i.e., product substrate particles, to pass out of the milling chamber in either a recirculation or discrete pass mode. Recirculation is often in the form of a dispersion such as a slurry, suspension, dispersion, or colloid of the substrate suspended in a fluid carrier phase that moves from the milling chamber into an often stirred holding vessel and thence back to the milling chamber, frequently with the aid of a pump. A separator or screen is effectively located at the outlet port of the milling chamber. Such means for simultaneous milling and media separation are referred to as "dynamic media separation".

In another method of continuous milling of a substrate, mills operating in a continuous mode can incorporate a means for retaining relatively large particles of the solid substrate being milled in the milling zone or milling chamber of the mill while allowing smaller particles of the substrate being milled, i.e., product substrate particles, as well as the milling media to pass out of the milling chamber in either a recirculation or discrete pass mode. In recirculation mode, the product substrate particles and the media suspended in a fluid carrier move from the milling chamber through the separator or screen into an often stirred holding vessel and thence back to the milling chamber, frequently with the aid of a pump.

In yet another method of continuous milling of a substrate, mills operating in a continuous mode can incorporate a means for retaining both relatively large particles of the solid substrate being milled and large size milling media in the milling chamber of the mill while allowing smaller particles of the substrate being milled, i.e., product substrate particles, as well as small size milling media to pass out of the milling chamber in either a recirculation or discrete pass mode. In recirculation mode, the product substrate particles and the small size media suspended in a fluid carrier move from the milling chamber through a separator or screen into an often stirred holding vessel and thence back to the milling chamber, frequently with the aid of a pump.

In a batch process, the milling media, the fluid carrier, and the substrate being milled remain in the vessel until the fractured substrate particles have been reduced to the desired size or to a minimum size achievable. The fluid carrier and the product substrate particles are then separated from the media particles with a separator or screen at the outlet port of the milling chamber.

Various techniques have been established for retaining media in media mills, including media separators such as rotating gap separators, screens, sieves, centrifugally-assisted screens, and similar devices to physically restrict passage of media from the mill. Retention of media arises because the dimensions of the milling media are larger than the dimensions of the openings through which the reduced size substrate particles can pass.

In batch processes employing ball mills (e.g. Abbe Ball Mills) or stirred ball mills (e.g. Union Process Attritor) separation of dispersion and milling media is performed after milling is complete, usually through a screen or sieve or filter sized smaller than the milling media. Typically, the screen is affixed to the milling vessel and slurry is removed by gravity drainage or pumped out of the vessel to pass through the filter. Alternatively, the slurry may be forced from the vessel by charging the vessel with compressed gas. However, the use of relatively large size milling media can impose a practical limitation to the final size of the substrate particles produced in the milling process.

In recent years there has been a transition to the use of small milling media in conventional media mill processes of solid substrates for the preparation of various paints, pigment dispersions, photographic, pharmaceutical dispersions, and the like. The advantages obtained with the use of smaller size media include faster rates of substrate particle size reduction and more rapid attainment of smaller substrate particle size distributions as products of the milling process, i.e., more efficient comminution. Improvements in conventional media mill designs such as in Netzsch LMC mills and Drais DCP mills have incorporated smaller screen opening dimensions that allow physical separation of larger milling media from substrate particles as small as 250 to 300 micrometers or less. However, even with the best machine designs available, it is generally not possible to use media smaller than about 250 to 300 micrometers due to separator screen plugging proximal to the milling chamber and unacceptable pressure build-up due to hydraulic packing of the media. Commonly, for commercial applications, a grinding media size of 350 micrometers is considered the practical lower limit for media particle retention due to media separator screen limitations.

The use of media that are smaller than the screen opening size in conventional media mills has permitted the reduction of solid substrates to particle sizes on the order of about 50 micrometers. For example, Czekai et al. in U.S. Pat. Nos. 5,513,803 and 5,718,388 disclose the use of ultrafine milling media for the preparation of fine particles useful in imaging elements and pigments. However, the mill media separator gaps were selected to be at least two to ten times the size of the smaller media such that both the smaller media and the reduced size substrate product particles could pass through the separator gaps in the mill. This resulted in a need for continuous addition of a mixture of smaller media and substrate to the milling chamber and continuous removal of a mixture of smaller media and reduced size substrate product from the milling chamber. In addition, removal of the substrate product from the smaller size milling media required a later separation step. Simultaneous use of a mixture of large and small size milling media wherein the larger size media were retained in the milling chamber and a smaller size media were not retained within the milling chamber still required a later step after milling to separate the smaller media from the milled substrate product.

Liversidge et al. in U.S. Pat. No. 5,145,684 and in European Patent Application 498,492 describe dispersible particles consisting of a drug substance or an x-ray contrast agent having a surface modifier adsorbed on the surface thereof in an amount sufficient to maintain an effective average particle size of less than about 400 nm. The particles are prepared by dispersing a drug substance or imaging agent in a liquid dispersion medium and wet grinding in the presence of rigid grinding media. Liversidge et al. do not suggest a continuous milling process using at least two size distributions of milling media wherein one size distribution is smaller that the openings in a media separator device in the milling chamber of a media mill and wherein the grinding media is separated from the pharmaceutical agent inside the milling chamber and the grinding media is retained in the milling chamber.

Bruno et al. in U.S. patent application Ser. No. 07/981,639 filed Nov. 25, 1992 entitled Method for Grinding Pharmaceutical Substances disclose polymeric grinding media for fine grinding pharmaceutical compositions.

U.S. Pat. No. 5,662,279 describes the milling of a slurry of a compound using rigid milling media to reduce the particle size of the compound. However, removal of the product from the milling media was done in a subsequent step by vacuum filtration through a removable filter probe attached to a conduit immersed in the slurry.

U.S. Pat. Nos. 5,470,583 and 5,336,507 disclose methods for preparation of nanoparticles using a charged phospholipid as a cloud point modifier.

U.S. Pat. No. 5,302,401 discloses compositions and methods for forming nanoparticles with a surface modifier and a cryoprotectant adsorbed thereon.

U.S. Pat. No. 5,478,705 discloses a process for the preparation of solid particles of a compound useful in photographic, electrophotographic, or thermal transfer imaging elements having an average particle size of less than 1 micron which comprises milling the compound in the presence of milling media comprising a polymeric resin.

U.S. Pat. No. 5,500,331 discloses a method of preparing submicron particles of a material, such as a pigment useful in paints or a compound useful in imaging elements, which comprises milling the agent in the presence of milling media having a mean particle size of less than about 100 microns. In a preferred embodiment, the milling media is a polymeric resin.

U.S. Pat. No. 5,518,187 discloses a method of preparing particles of a drug substance or diagnostic imaging agent that comprises grinding the drug substance or imaging agent in the presence of grinding media comprising a polymeric resin. It further discloses a method of preparing particles of a drug substance or a diagnostic imaging agent by grinding with rigid grinding media to reduce said particles to submicron size, wherein said grinding media has a substantially spherical shape, has a particle size range of 0.1 to 3 mm and comprises a polymeric resin.

U.S. Pat. No. 5,534,270 discloses a method of preparing sterilized nanoparticulate crystalline drug particles comprising the steps of providing a drug substance having a solubility in water of less than 10 mg/ml; depyrogenating rigid grinding media having an average particle size less than 3 mm; mixing and autoclaving the drug substance and rigid grinding media; and adding a surface modifier to the autoclaved drug substance and rigid grinding media to a dispersion medium such as water and wet grinding the drug substance sufficiently to maintain an effective average particle size of less than 400 nm. The rigid grinding media is selected from the group consisting of zirconium silicate beads, zirconium oxide stabilized with magnesia and glass beads.

U.S. Pat. No. 5,657,931 discloses a process for the preparation of a fine solid particle aqueous dispersion of a substantially water-insoluble non-polymeric organic compound useful in imaging which process comprises forming a coarse aqueous slurry of solid particles of said compound and an amphipathic water-soluble or water-dispersible block polymeric dispersant having an HLB number of at least 8 and then milling said slurry for a period of time sufficient to provide particles of the desired particle size of less than 0.5 micron.

U.S. Pat. No. 5,704,556 discloses a process for rapidly producing colloidal particles, the process comprising providing a feedstock slurry having an average particle size less than one micron to a stirred media mill, the slurry including from about 5 to 10 percent by weight dispersant; and a total solids of less than about 50 percent by weight in a low viscosity fluid; providing ceramic beads selected from zircon, glass and yttrium toughened zirconium oxide less than 100 microns in diameter in the mill; filling the mill to a volume in excess of 90%; operating the mill at tip speeds at least 20 meters/sec; and limiting the residence time to less than about two minutes, thereby producing particles having an average particle size less than about 0.1 micron from the feedstock. In one aspect, the diameter of the ceramic beads is no more than about one hundred times the average particle size of the feedstock particles.

U.S. Pat. No. 5,862,999 discloses a method of grinding particles of a therapeutic or diagnostic agent in which the agent is ground in the presence of rigid grinding media having a mean particle size of less than about 100 microns. The therapeutic or diagnostic agent particles produced by the grinding process have an average particle size of less than about 500 nm.

U.S. Pat. No. 5,902,711 discloses a process of forming milled solid particles of an electrophotographic toner pigment compound comprising milling solid particles of the compound in a liquid organic medium continuous phase in the presence of polymeric milling media to reduce the average size of the compound particles. The liquid continuous phase such as an ethylenically unsaturated polymerizable monomer comprises a solvent for the milling media polymer in the uncrosslinked form and the milling media is crosslinked sufficiently to prevent 50 volume per cent swelling of the polymeric milling media in the liquid continuous phase within four hours at 25° C. The polymeric milling media can have a mean particle size of less than about 100 micrometers in the unswelled state prior to addition to the liquid organic continuous phase. The compound particles are milled to an average particle size of less than 100 nm. The milling media polymer comprises polymerized styrene and divinylbenzene monomers.

International Patent Application WO 99/39700 describes the preparation of submicron nanoparticles from a pharmacologically active principle and a composite material consisting of at least one lipidic substance and at least one amphiphilic substance using high pressure homogenization to form a microemulsion of the composite material at a temperature higher than the melting temperature of at least one of the materials forming the composite and in the presence of one or more aqueous surfactants as surface active substances and then cooling the microemulsion to form a dispersion of solid particles.

U.S. Pat. No. 5,922,355 discloses a method for preparing submicron size microparticles by particle size reduction methods in which a solid material is reduced in size over a period of time while continuously below the melting point of the material or by precipitation while the particles are stabilized with phospholipids as surface active substances in combination with other surface modifiers to control growth of particle size and enhance storage stability. The use of one or more surface modifiers in addition to a phospholipid provides volume weighted mean particle size values that are much smaller than what can be achieved using phospholipid alone without the use of an additional surface active substance (surfactant) with the same energy input while providing compositions resistant to particle size growth on storage. The phospholipid and the surfactant are both present at the time of particle size reduction.

U.S. Pat. No. 5,700,471 discloses a process for the micronization of compounds having low solubility in water by exposing such compounds briefly to a temperature above their respective melting points, dispersing them with turbulence in an aqueous or organic phase, and subsequently cooling the phase to form a fine particle dispersion.

U.S. Pat. No. 4,880,634 describes a method of production of an excipient system containing a pharmacologically active substance for peroral administration comprised of lipid nano-pellets in an aqueous, colloidal suspension. The method comprises forming a melt of a mixture of at least one surfactant, a pharmacologically active substance, and at least one lipid, dispersing the molten mixture within an aqueous solution at a temperature above the melting point of the lipid to form lipid nano-pellets, and cooling the suspension below the melting point of the lipid. In the process, a pharmacologically effective substance is thoroughly dissolved in the lipid or mixture of lipids during the preparation of the lipid nano-pellets.

U.S. Pat. Nos. 5,091,187 and 5,091,188 discloses water-insoluble drugs rendered injectable as aqueous dispersions of phospholipid-coated microcrystals. The crystalline drug is reduced to 50 nm to 10 micrometers by sonication or other processes inducing high shear in the presence of phospholipid or other membrane-forming amphipathic lipid.

WO 97/14407 discloses particles of water-insoluble biologically active compounds including drugs with an average size of 100 nm to 300 nm that are prepared by dissolving the compound in a solution and then spraying the solution into compressed gas, liquid, or supercritical fluid in the presence of appropriate surface modifiers.

The advantages in drug delivery of water-insoluble drugs formulated as small particles have been described in a review by Pace et al., "Novel injectable formulations of insoluble drugs," in Pharmaceutical Technology, March 1999 the contents of which are hereby incorporated by reference.

It would be desirable to provide an improved milling and media separation process, particularly for use with media smaller than 350 micrometers, wherein the milling media are retained in the milling chamber and milled substrate particles in a carrier fluid are separated from the media.

It is an object of the invention to provide a milling process capable of making ultra-fine particle dispersions with weight average particle sizes less than 100 micrometers.

It is a further object to provide a milling process which enables the use of milling media less than 100 micrometers in weight average size whereby such media is separated from ultra-fine particle dispersions without plugging of a media separator.

It is a further object to provide a milling process in which milling media is not removed from the milling vessel to accomplish media/dispersion separation.

BRIEF SUMMARY OF THE INVENTION

We have discovered a milling process for milling a solid substrate in the milling chamber of a media mill in the presence of a media separator of screen having openings of size $S_0$ wherein the above objectives are achieved. In this invention, the milling media comprise a mixture of large size media and small size media. The large size media have a size $S_1$ all of which are larger than $S_0$; they will not pass through the separator and thus will remain in the milling chamber. The small size media have a size $S_2$ that is at least smaller than $S_1$ and is preferably smaller than $S_0$. In this invention, large size media optionally in the presence of a fluid carrier are added to the milling chamber. The large size media form a depth filter comprising an array of contacted milling media and voids, channels, and spaces among the milling media particles distributed, stacked or layered on the exit screen of the milling chamber. The small size media are larger than the voids, channels, and spaces of the depth filter and thus will not pass through the depth filter even though they are smaller than the openings in the separator. Subsequently, a conglomerate comprising a solid to be milled, fluid carrier, small size media and optionally additional large size media are added to the milling chamber either directly or by being pumped from a reservoir or holding tank that is optionally stirred, and the solid is milled to produce very small particles of solid substrate. The very small particles are smaller than the smallest media size present in the milling chamber. During the milling process, at least a portion of the depth filter proximal to the exit screen is not agitated. The large media particles and the small media particles will not pass through the depth filter and remain in the milling chamber during and after the milling process. The fluid carrier and the very small particles of milled product substrate which are small enough to pass through the spaces, voids, and channels in the depth filter can pass out of the milling chamber and be separated from the milling media. The very fine particles are obtained free of milling media as a dispersion in the fluid carrier.

In another embodiment of the milling process of this invention, large size media of size $S_1$ larger than $S_0$ or a distribution of large size media having an average size $S_1$ in which all are larger than $S_0$ is added to the milling chamber of a media mill. The large size media are allowed to form a depth filter at an exit screen in the milling chamber of the media mill. The depth filter comprises one to several layers of large size media on the exit screen having openings of size $S_0$. An agglomerate comprising a solid substrate to be milled and small size milling media of size $S_2$ smaller than $S_0$ or a distribution of small size media having an average size $S_2$ smaller than $S_0$ or a mixture of said small size media and additional large size media is added to the milling chamber. The solid substrate is mechanically milled by the media to produce very small particles of substrate product. The very small milled product substrate particles are continuously removed from the milling chamber as a dispersion in the fluid carrier and are separated from both the small and the large media by passage through the depth filter together with the fluid carrier. During the milling process, at least one layer of large media of the depth filter remains substantially non-agitated or undisturbed by the movement of any other milling media or substrate particles or fluid carrier in the milling chamber. Neither the large size milling media nor the small size milling media are removed from the milling chamber by passing through the openings in the separator. Fluid carrier that passed through the depth filter can be replaced with additional fluid carrier or be recirculated back into the media mill optionally in the form of a fluid carrier dispersion of very small milled substrate particles.

In accordance with one embodiment of the invention, we have discovered a process for preparing a dispersion of solid particles of a milled substrate in a fluid carrier comprising the steps of:

(a) providing a plurality of large size milling media to the milling chamber of a media mill and forming a depth filter therefrom on an exit screen or separator in the milling chamber;

(b) adding to said milling chamber a plurality of small size milling media optionally containing additional large size milling media, a conglomerate of a solid substance comprising a substrate to be milled and optionally one or more than one surface active substance, and a fluid carrier;

(c) milling said conglomerate in said milling chamber to produce very small milled substrate product particles; and (d) separating said milled substrate particles suspended in said fluid carrier from the media through said depth filter; wherein:

the exit screen comprises openings of size $S_0$;

the large size media have a size distribution $S_1$ of which all are larger than $S_0$;

the small size media have a size distribution $S_2$ which are smaller than $S_0$;

the very small milled substrate particles have a size distribution $S_3$ and are smaller than all of the small media; and the large size media and the small size media are retained in the milling chamber.

In another aspect of this invention, the milling media comprise a mixture of large size media and small size media. The large size media have a size $S_1$ all of which are larger than $S_0$; they will not pass through the separator and thus will remain in the milling chamber. The small size media have a size $S_2$ that is at least smaller than $S_1$ and is preferably smaller than $S_0$. In this invention, large size media optionally in the presence of a fluid carrier are added to the milling chamber. The large size media form a depth filter comprising an array of contacted milling media and voids, channels, and spaces among the milling media particles distributed, stacked or layered on the exit screen of the milling chamber. The small size media are larger than the voids, channels, and spaces of the depth filter and thus will not pass through the depth filter even though they are smaller than the openings in the separator. Subsequently, a conglomerate comprising a solid to be milled, fluid carrier, small size media and optionally additional large size media are added to the milling chamber, and the solid is milled to produce very small particles of solid substrate. The very small particles are smaller than the smallest media size present in the milling chamber. During the milling process, at least a portion of the depth filter proximal to the exit screen is not agitated. The large media particles and the small media particles will not pass through the depth filter and remain in the milling chamber during and after the milling process. The fluid carrier and the very small particles of milled product substrate which are small enough to pass through the spaces, voids, and channels in the depth filter can pass out of the milling chamber and be separated from the milling media. The very fine particles are obtained substantially free of milling media as a dispersion in the fluid carrier.

In another embodiment of the milling process of this invention, large size media of size $S_1$ larger than $S_0$ or a distribution of large size media having an average size $S_1$ in which all are larger than $S_0$ is added to the milling chamber of a media mill. The large size media are allowed to form a depth filter at an exit screen in the milling chamber of the media mill. The depth filter comprises one to several layers of large size media on the exit screen having openings of size $S_0$. An agglomerate comprising a solid substrate to be milled and small size milling media of size $S_2$ smaller than $S_0$ or a distribution of small size media having an average size $S_2$ smaller than $S_0$ or a mixture of said small size media and additional large size media is added to the milling chamber. The solid substrate is mechanically milled by the media to produce very small particles of substrate product. The very small milled product substrate particles are continuously removed from the milling chamber as a dispersion in the fluid carrier and are separated from both the small and the large media by passage through the depth filter together with the fluid carrier. During the milling process, at least one layer of large media of the depth filter remains substantially non-agitated or undisturbed by the movement of any other milling media or substrate particles or fluid carrier in the milling chamber. Essentially none of the large size milling media or the small size milling media are removed from the milling chamber by passing through the openings in the separator. Fluid carrier that passed through the depth filter can be replaced with additional fluid carrier or be recirculated back into the media mill optionally in the form of a fluid carrier dispersion of very small milled substrate particles.

In accordance with this embodiment of the invention, we have discovered a process for preparing a dispersion of solid particles of a milled substrate in a fluid carrier comprising the steps of:

(e) providing a plurality of large size milling media to the milling chamber of a media mill and forming a depth filter therefrom on an exit screen or separator in the milling chamber;

(f) adding to said milling chamber a plurality of small size milling media optionally containing additional large size milling media, a conglomerate of a solid substance comprising a substrate to be milled and optionally one or more than one surface active substance, and a fluid carrier;

(g) milling said conglomerate in said milling chamber to produce very small milled substrate product particles; and (h) substantially separating said milled substrate particles suspended in said fluid carrier from the media through said depth filter; wherein:

the exit screen comprises openings of size $S_0$;

the large size media have a size distribution $S_1$ of which all are larger than $S_0$;

the small size media have a size distribution $S_2$ which are smaller than $S_0$;

the very small milled substrate particles have a size distribution $S_3$ and are smaller than all of the small media; and the large size media and the small size media are essentially retained in the milling chamber.

In preferred embodiments of the invention, milling is performed by high speed mixing of the solid conglomerate as a dispersion in the fluid carrier with the media in the milling chamber.

By this process, milling of solid substrate and separation of milled substrate from the milling media are combined in that the media are used for both milling and separation steps. Media separator screen plugging during or after milling is eliminated. Unlike conventional media separation processes, there is minimal loss of dispersion associated with use of a depth filter comprised of large size media. The depth filter and screen may be sized to accomplish both media separation and purification of the dispersion in one step.

While the process in applicable to the wide variety of commercially available media sizes and is useful for milling a wide variety of substrate materials including those heretofore mentioned, it is particularly useful for milling substrates with extremely small media such as media of size less than 350 micrometers which may be effectively separated from milled substrate product particles using this process. Milling media greater than 350 micrometers may be used as small sized media in the presence of larger size media that can form a depth filter on the exit screen of the milling chamber through which the smaller media do not pass.

Depending on the intended use and application, large size milling media can range in size up to the largest size media available for use in a media mill. In one aspect, large size media can be selected from cannon balls, steel shot, ball bearings, and the like. Large size media can have average sizes such as 10 cm, 5 cm, 2 cm, 1 cm, 50 mm, 10 mm, 5 mm, 2 mm, 1 mm, 0.5 mm, and 0.2 mm. Smaller sized milling media can be selected to be smaller than the larger size milling media by a factor of 0.5 times, more preferably by a factor of 0.3 times.

The milling media need not be removed from the milling chamber, thereby minimizing handling of the milled substrate and the media and minimizing chances for contamination.

In a preferred embodiment, a substrate material can be a pharmaceutical compound such as a drug or formulation of a drug useful in treatment of a disease or as a diagnostic agent. The pharmaceutical compound or formulation can be milled in a batch or continuous process using a mixture of small and large particle milling media to obtain submicrometer substrate particles dispersed in a fluid carrier.

It is another advantageous feature of this invention that there is provided a milling method which enables the use of ultra-fine milling media, e.g., of a particle size less than 350 micrometers, in a continuous or batch milling process.

It is an advantage that the depth filter restricts the exit of both the larger and smaller size distribution of media during milling but permits the passage of the very small particles of milled substrate, thereby facilitating both grinding of a solid substrate and separation of the very small substrate product particles from both the large and small size distributions of milling media and from residual large particles of substrate that will not pass through the depth filter.

It is a particularly advantageous feature of this invention that there is provided a method of preparing extremely fine particles of pharmaceutical agents, particularly poorly water-soluble or water-insoluble therapeutic and diagnostic agents.

It is another advantageous feature of this invention that there is provided a grinding method which enables the use of ultra-fine grinding media, e.g., of a particle size less than 350 micrometers, in a grinding process.

Other advantageous features will become readily apparent upon reference to the following description of preferred embodiments when in read in light of the accompanying drawings.

DETAILED DESCRIPTION OF THE INVENTION

Figure 1:
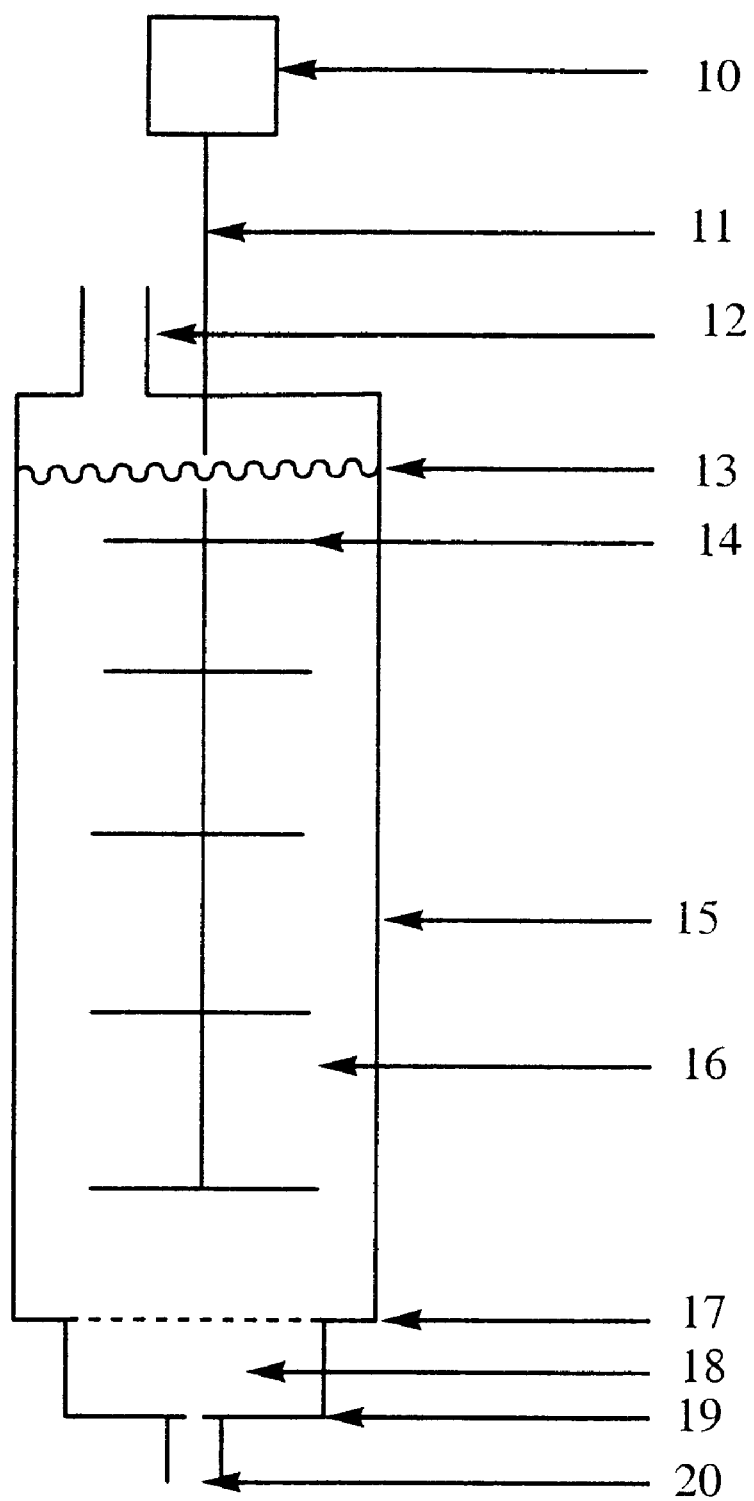
FIG. 1 is a schematic drawing of a media mill useful in milling a substrate in a batch process in the presence of a depth filter comprised of large size milling media.

In accordance with this invention, a process is disclosed for preparing a dispersion of solid particles of a milled substrate in a fluid carrier comprising the steps of:

(a) providing a plurality of large size milling media to the milling chamber of a media mill and forming a depth filter therefrom on an exit screen or separator in the milling chamber;

(b) adding to said milling chamber a plurality of small size milling media optionally containing additional large size milling media, a conglomerate of a solid substance comprising a substrate to be milled and optionally one or more than one surface active substance, and a fluid carrier;

(c) milling said conglomerate in said milling chamber to produce very small milled substrate product particles; and (d) separating said milled substrate particles suspended in said fluid carrier from the media through said depth filter; wherein:

the exit screen comprises openings of size $S_0$;

the large size media have a size distribution $S_1$ of which all are larger than $S_0$;

the small size media have a size distribution $S_2$ which are smaller than $S_0$;

the very small milled substrate particles have a size distribution $S_3$ and are smaller than all of the small media; and the large size media and the small size media are retained in the milling chamber.

We have discovered a milling process for milling a solid substrate in the milling chamber of a media mill in the presence of a media separator of screen having openings of size $S_0$ wherein the above objectives are achieved. In this invention, the milling media comprise a mixture of large size media and small size media. The large size media have a size $S_1$ all of which are larger than $S_0$; they will not pass through the separator and thus will remain in the milling chamber. The small size media have a size $S_2$ that is at least smaller than $S_1$ and is preferably smaller than $S_0$. In this invention, large size media optionally in the presence of a fluid carrier are added to the milling chamber. Some (for example, from about 1% to about 99% of the total number, preferably from about 1% to about 50% of the total number) of the large size media form a depth filter comprising an array of contacted milling media and voids, channels, and spaces among the milling media particles distributed, stacked or layered on the exit screen of the milling chamber. The small size media are larger than the voids, channels, and spaces of the depth filter and thus are trapped by the depth filter even though they are smaller than the openings in the separator. In a preferred aspect, the small size media will not pass through the depth filter. Subsequently, a conglomerate comprising a solid to be milled, fluid carrier, small size media and optionally additional large size media are added to the milling chamber, and the solid is milled to produce very small particles of solid substrate. The very small particles are smaller than the smallest media size present in the milling chamber. During the milling process, at least a portion of the depth filter proximal to the exit screen is not agitated. The large media particles and the small media particles are restricted by the depth filter and are substantially held in the milling chamber during and after the milling process. The fluid carrier and the very small particles of milled product substrate which are small enough to pass through the spaces, voids, and channels in the depth filter can pass out of the milling chamber and be separated from the milling media. The very fine particles are obtained substantially free of milling media as a dispersion in the fluid carrier.

In a preferred aspect, the exit screen in the milling chamber comprises openings of less than 1 millimeter.

When micron and submicron particles are produced in the various embodiments of the process of this invention, preferably a surface active agent or surface modifier is added to stabilize the very small particles. The surface active agent can be added prior to the start of the milling process, during the milling process, or after the milling process is completed. Preferably, the surface active agent is present during the size reduction milling process. The surface active agent can be completely or partially soluble in the fluid or be present as a separate phase such as a liquid or a solid during the milling process.

In a preferred aspect, the large media particles and the small media particles will not pass though the depth filter and remain held in the milling chamber during and after the milling process, and the very fine particles are obtained free of milling media as a dispersion in the fluid carrier.

In another embodiment of the milling process of this invention, large size media of size $S_1$ larger than $S_0$ or a distribution of large size media having an average size $S_1$ in which all are larger than $S_0$ is added to the milling chamber of a media mill. A number of these large size media, for example, from about 1% to about 50% of the number of the large size media are allowed to form a depth filter at an exit screen in the milling chamber of the media mill. The depth filter comprises one to several layers (preferably from 2 to about 100 layers, and more preferably from about 3 to about 25 layers) of large size media on the exit screen having openings of size $S_0$. An agglomerate comprising a solid substrate to be milled and small size milling media of size $S_2$ smaller than $S_0$ or a distribution of small size media having an average size $S_2$ smaller than $S_0$ or a mixture of said small size media and additional large size media is added to the milling chamber. The solid substrate is mechanically milled by the media to produce very small particles of substrate product. The very small milled product substrate particles are continuously removed from the milling chamber as a dispersion in the fluid carrier and are separated from both the small and the large media by passage through the depth filter together with the fluid carrier. During the milling process, at least one layer of large media of the depth filter remains substantially non-agitated or undisturbed by the movement of any other milling media or substrate particles or fluid carrier in the milling chamber. In a preferred aspect, neither the large size milling media nor the small size milling media are removed from the milling chamber by passing through the openings in the separator. Fluid carrier that passes through the depth filter can be replaced with additional fluid carrier alone or with additional fluid carrier containing a dispersion of substrate to be milled optionally containing milled substrate, or it can be recirculated back into the media mill optionally in the form of a fluid carrier dispersion of very small milled substrate particles.

In preferred embodiments, $S_1$ is at least 1.2 times larger than $S_1$, preferably $S_1$ is at least 1.5 times larger than $S_0$, and more preferably $S_1$ is at least 3.0 times larger than $S_0$. In preferred embodiments, $S_2$ is at most 0.99 times the size of $S_0$, preferably $S_2$ is at most 0.95 times the size of $S_0$, and more preferably $S_2$ is at most 0.85 times the size of $S_0$.

In preferred embodiments of the invention, milling is performed by high speed mixing of the solid conglomerate as a dispersion in the fluid carrier with the media in the milling chamber.

The media milling and separation process of this invention comprises the milling of a solid substrate to produce a dispersion of very small product substrate particles in a fluid carrier and the separation of the very small product substrate particles and fluid carrier from the media. The process can be a batch process or a continuous process.

With reference to FIG. 1, one embodiment of the process of this invention can be carried out as follows. FIG. 1 depicts a media mill useful in this invention configured for a batch milling and separation process. In FIG. 1, large size milling media (not shown) and fluid carrier are added to the milling chamber 16 of media mill 15 through entry port 12 and form a depth filter in region 18 proximal to exit screen 19. During this charging of the mill, the agitator 14 can optionally be in operation, and the exit port 20 can be open to allow fluid carrier to exit from the mill or be closed to contain the fluid carrier. Optionally, a secondary larger screen 17 comprising openings through which the large size media can pass can be present in the mill. The milling chamber is then charged with a conglomerate comprising a solid substrate to be milled, small size milling media, and optionally additional fluid carrier. The exit port 20 of the milling chamber is closed and the mill is charged to a level 13. The contents of the mill are agitated or stirred, preferably at a high speed or with high acceleration and deceleration, by agitator 14 that is driven by motor 10. When the solid substrate is milled to a very fine particle size that will pass through the depth filter, the exit port 20 is opened and the very fine product particles of milled solid substrate as a dispersion in the fluid carrier are removed, optionally under pressure or by means of a pump from the milling chamber by passing through the depth filter. The milling media remain in the milling chamber, and the very fine product substrate particles are isolated substantially free of milling media as a dispersion in the fluid carrier. Optionally, fluid carrier can be added to the mill to wash out the remaining dispersion.

In a preferred aspect, the milling media remain in the milling chamber, and the very fine product substrate particles are isolated free of milling media as a dispersion in the fluid carrier.

Figure 2:
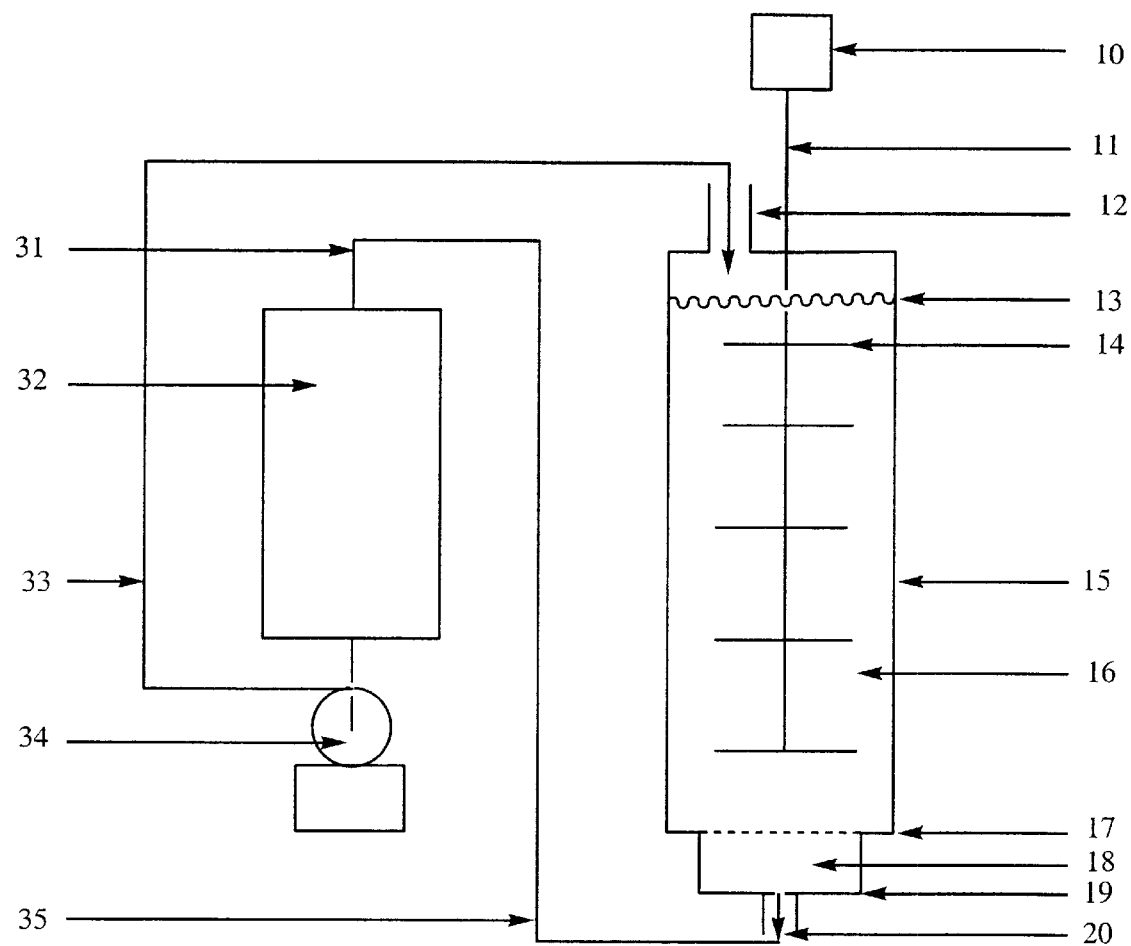
FIG. 2 is a schematic diagram of a media mill useful in milling a substrate in a continuous process in the presence of a depth filter comprised of large size milling media.

With reference to FIG. 2, another embodiment of the process of this invention can be carried out as follows. FIG. 2 depicts a media mill useful in this invention configured for a continuous milling and separation process. In FIG. 2, large size milling media (not shown) and fluid carrier are added to the milling chamber 16 of media mill 15 through entry port 12, and a number of the large media form a depth filter in region 18 proximal to exit screen 19. During this charging of the mill, the agitator 14 can optionally be in operation, and the exit port 20 can be open to allow fluid carrier to exit from the mill or be closed to contain the fluid carrier. Optionally, a secondary larger screen 17 comprising openings through which the large size media can pass can be present in the mill. The milling chamber is then charged with a conglomerate comprising a solid substrate to be milled, small size milling media, and optionally additional fluid carrier. Additional large size milling media can be added with the conglomerate or separately. The exit port 20 of the milling chamber is not closed and the mill is charged to a level 13. Fluid carrier is transferred by means of a piping system 35 with the aid of a pump 34 to a holding tank 32 via inlet port 31. The fluid carrier is pumped from the holding tank via the piping system 33 back to the inlet port 12 of the media mill. The contents of the mill are agitated or stirred, preferably at a high speed or with high acceleration and deceleration, by agitator 14 that is driven by motor 10. Fluid carrier is continuously recirculated from the milling chamber through the depth filter to the holding tank. As the solid substrate is milled to a very fine particle size that will pass through the depth filter, the dispersion of the product particles is continuously transferred to the holding tank. This recirculation can be continued until a minimum or a desired substrate particle size is obtained. Optionally, the dispersion of the very fine product particles can be removed from the holding tank, the particles can be isolated or the dispersion can be concentrated by removal of the fluid and the fluid can be returned to the milling chamber (not shown) to collect additional very fine product particles to transfer as a dispersion to the holding tank. At the end of the process, the residual very fine product particles of milled solid substrate remaining in the media can be transferred to the holding tank as a dispersion in the fluid carrier, optionally under pressure or by means of a pump from the milling chamber by passing through the depth filter. Essentially all milling media remain in the milling chamber, and the very fine product substrate particles are isolated substantially free of milling media as a dispersion in the fluid carrier.

In a preferred aspect, all of the milling media remain in the milling chamber, and the very fine product substrate particles are isolated free of milling media as a dispersion in the fluid carrier.

The media milling process uses a separator or screen at the exit port of the milling chamber to maintain media particles in the milling vessel while permitting the very small product particles (such as surface active agent stabilized very small product particles) and the fluid carrier to exit the milling vessel. Large milling media particles are added to the milling chamber and form a depth filter of several (for example from 1 to 25 or more) layers of particles on the exit screen. The depth filter contains spaces, voids and channels that restrict passage of the large and small size milling media as well as solid substrate that has not been milled to a desired very small size. However, the spaces, voids and channels will permit passage of fluid carrier and very small sized milled product substrate particles dispersed in the fluid carrier.

Figure 3:
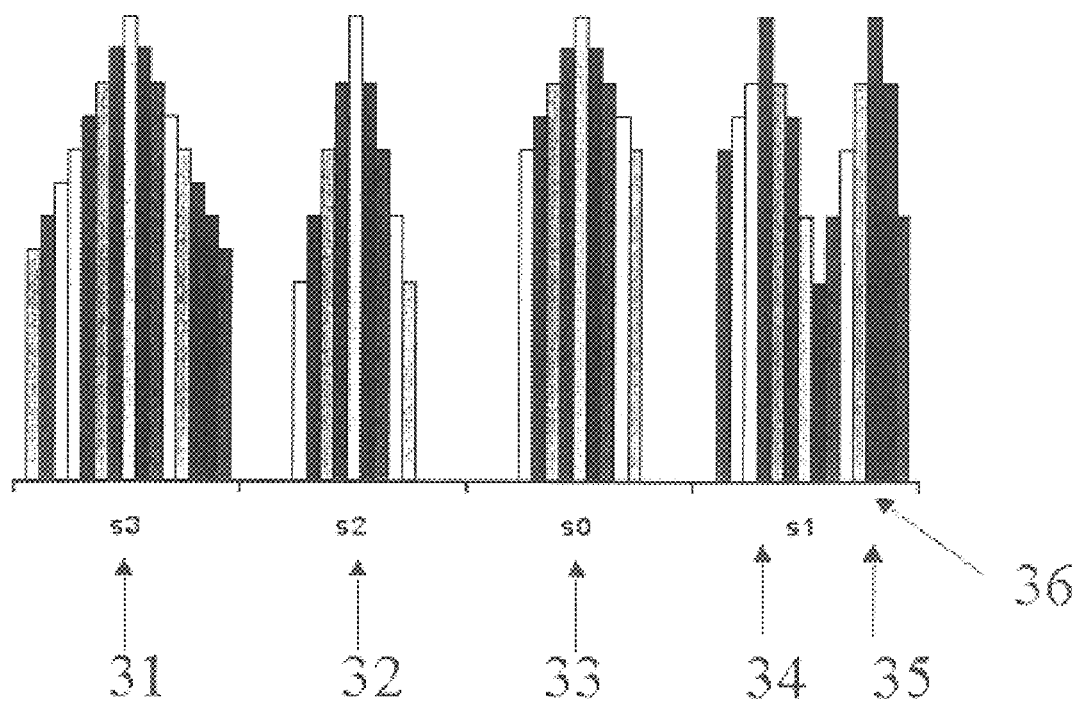
FIG. 3 is a graph representing relative size distributions of small size milling media, large size milling media, and openings in a separator or screen in the milling chamber of a media mill.

With reference to FIG. 3, an embodiment of the size distribution relationships among the openings in the separator, the large size milling media, the small size milling media, and the very fine milled product substrate particles of this invention is exemplified. In FIG. 3, representative relative size distributions for very small milled product substrate particles $S_3$, for small size milling media $S_2$, for openings $S_0$, and for large size milling media $S_1$ are displayed on axis 36 in which relative size increased from left to right. The representative heights of the distributions are each normalized and do not represent the absolute frequency of their occurrence in the process of this invention. The size distribution of large milling media is shown as being a representative bimodal distribution comprising a mixture of a large size distribution 34 and a larger size distribution 35. However, the large size milling media distribution can be a mixture of any size milling media that are larger than the distribution 33 provided the mixture of large media will form a depth filter according to this invention. In the current distribution represented by the figure, both 34 and 35 are larger in size than any portion of the size distribution 33 of openings in the separator screen. The size distribution 32 of the small size milling media is depicted as an approximately normal size distribution but it can comprise any mixture of sizes in the size region smaller than distribution 33 of the separator openings to greater than distribution 31 of the very fine particle size distribution. The size distribution of the openings in the separator screen is represented by distribution 32. All members of the size distribution are smaller than the all members of the large milling media size distribution that comprise the depth filter, and in this embodiment are larger than all members of the size distribution of the small milling media. The size distribution of the very small product substrate particles is represented as 31. All members of the very small product substrate particle size distribution 31 are smaller than all members of small milling media distribution 32. Size distribution 31 will depend on the size of the channels and void spaces in the depth filter which will depend in large part on the size distribution of the large size milling media and the size of the depth filter, i.e., the number of layers in the depth filter.

The screen or separator in the media mill comprises an array of openings of size $S_0$. The openings may be in the form of a separator gap. The array can be a series of substantially parallel slits; a mesh or screen or series of separated geometric openings such as squares, rectangles, triangles, rhombohedra or other quadrilateral shapes, circles, ovals, and openings of irregular shape. The openings can be of substantially uniform shape, or they can be a combination of shapes such as slits and arrays of squares to form a mesh. In the case of separator openings being slits, the distance between the long parallel edges of the slit is considered a measure of $S_0$. In this case where milling media comprise spherical beads of diameter larger than $S_0$, such beads would not pass through the slit opening, but spherical milling beads of diameter smaller than $S_0$ could pass through the opening slit in the absence of a depth filter. In the case of cylindrical milling media where the height of the cylinder is shorter than the diameter, the height dimension determines if the media will pass through the separator slit: cylindrical media with heights larger than $S_0$ will not pass through the separator while cylindrical media with heights smaller than $S_0$ will pass through the separator. Conversely, in the case of cylindrical milling media where the height of the cylinder is longer than the diameter, similar to the spherical media, the diameter dimension determines if the media will pass through the separator slit. In the case of a separator comprised of an array of geometric shapes such as a mesh or screen of squares, rectangles, circles and the like, or a plate such as a stainless steel plate containing holes of size $S_0$, a depth filter will form according to this invention if the large size media will not pass through the openings in the array.

The openings can be of substantially uniform size $S_0$ or they may comprise a distribution of openings of average size $S_0$. In a preferred embodiment of this invention, the large size milling media will not pass through the largest opening in an array of average size $S_0$.

Large size milling media can be substantially uniform or may be a mixture of sizes and shapes to form a distribution of sizes. The average size is herein defined as $S_0$. In a preferred embodiment, all members of the large size milling media distribution are of a size larger than the largest opening in the distribution of openings defined herein as $S_0$ and no large milling media particle will pass through any opening in the separator or screen once a depth filter is established.

Sufficient numbers of large size milling media are required so that a depth filter is formed on all portions of the separator screen that contain openings. Use of enough large size milling media to form at least one layer of a depth filter is required. Use of more large size milling media than required to form a single layer is preferred.

In one aspect, a depth filter can be formed by adding a mixture of small size milling media and large size milling media and fluid carrier to a media mill and operating the mill in a continuous or recirculation mode. In this process, small size media can pass through the openings in the separator while large size milling media will not pass through the openings. After a time, small media that are positioned proximal to the openings will be carrier through the openings and will eventually be replaced in proximity to the separator openings by large size media that will not pass through the openings. Thus, at least one layer, i.e. a first layer, of large size milling media will form or build up or become established adjacent to the separator screen. Additional layers comprising mixtures of large size and small size milling media will then build up on the first layer to form a depth filter. Preferably the volume fraction of small media in this aspect is less than 50% of the total volume fraction of the large and small media. The presence of small media in lower layers of the depth filter will alter the void spaces and channels in the depth filter and depending on the relative sizes of the small and large media and on the volume percentage of each can provide increased or decreased flow rates through the depth filter.

Small size milling media can be substantially uniform or may be a mixture of sizes and shapes to form a distribution of sizes. The average size is herein defined as $S_2$. All members of the small size milling media distribution are of a size such that they will pass through the openings in the separator in the absence of a depth filter.

In one embodiment of this invention, the depth filter can comprise large size milling media throughout, i.e., all media in the depth filter are large size media. In another embodiment of this invention, the depth filter can comprise large size milling media proximal to the separator screen for from one to about 25 layers and a mixture (up to 50% by volume) of large size milling media and small size milling media. In a preferred aspect up to half the depth of the depth filter that is not comprised of large media in from 1 to about 25 layers proximal to the exit screen can be a mixture of large and small sized media. In this embodiment, all media in the depth filter proximal to the screen are large size media (e.g., 1 to about 25 layers) and the composition of the depth filter transitions to a mixture of from 99% of large media and 1% of small media to about 20% of large media to about 80% of small media in the direction toward the interior of the milling chamber. In this embodiment, media are substantially or completely restricted from passing through the separator.

A preferred depth of the depth filter is at least 4 layers of large size milling media.

Figure 4:
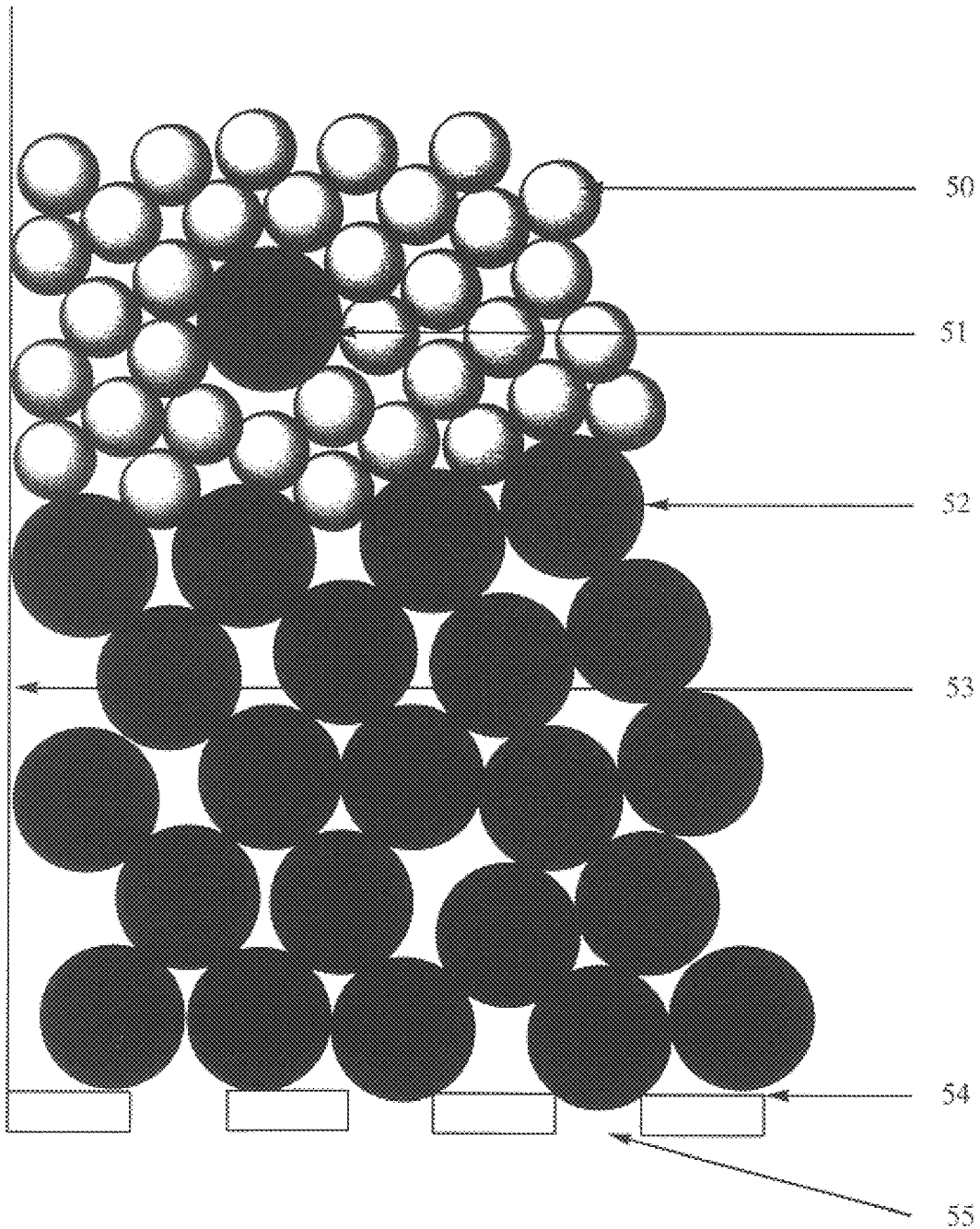
FIG. 4 is a schematic diagram of a depth filter of this invention comprising large size milling media that restricts passage of small size milling media through the openings of the separator screen but allows passage of very small milled substrate product particles in a fluid carrier through the separator screen.

With reference to FIG. 4, process of this invention embodying the formation and action of the depth filter comprising large size milling media can be further explained. FIG. 4 is a schematic diagram representing a portion of a depth filter of this invention proximal to a separator screen 54 having openings 55 and being adjacent to a wall 53 of the milling vessel to which the separator abuts or to which it is attached. The remainder of the depth filter and separator that extend to the opposite side of the milling vessel are not shown. The depth filter in this figure is comprised of substantially spherical large beads 52 in contact with adjacent large beads. Between and among the large beads are spaces, voids, and channels. Small size milling media 50 as well as additional large size milling media such as 51 can deposit on top of the depth filter and do not pass through the channels, voids and spaces. Milled product substrate particles (not shown) are smaller than all of the small size media and are small enough to pass through the spaces, channels and voids as a dispersion in the fluid carrier. The fluid carrier can pass through the depth filter with and without the very fine product particles.

In the process of this invention, large size milling media are retained proximal to the exit screen in the depth filter, and small size milling media deposit above the large size milling media in the depth filter. Kinetic energy transfer from the agitator in the mill and collisions among the elements present in the milling caused by the energy transfer from the agitator can cause the smaller milling media as well as unmilled or partially milling solid substrate to deposit on the depth filter. Deposited elements can subsequently become resuspended in the fluid carrier such as a result of kinetic energy transfer among moving and stationary elements in the mill.

In order to maintain the large milling media particles in the milling chamber, the large particles must be greater in size than the openings in the separator or screen. If the large milling particles are the same size as the screen openings, the screen can plug. If the large milling particle size is undesirably smaller than the screen openings, the particles can exit the milling vessel with the fluid carrier. Additionally, the subsequently added small size milling particles will pass through the screen in the absence of a depth filter. Preferably the large milling particle sizes are about 2 to 3 times larger than the screen openings.

This invention involves the simultaneous use of large size milling particles which are larger than the separator or screen openings and of small size milling particles which are smaller than the openings. Preferably, no milling particles of the size range of the screen openings are included in the milling particles that comprise the depth filter layer proximal to the screen openings. The milling particle size distribution will be at least bimodal consisting of some particles which are larger than the screen openings and some particles which are smaller than the screen openings. The very small particles of milled product substrate are all smaller than all of the small size milling media.

The use of more than two size distributions of milling media such as three or more size distributions of milling media, i.e. the use of polymodal size distributions of milling media are contemplated. An example of a polymodal size distribution of milling media includes a small size distribution which is smaller than $S_0$, together with a first large size and a second large size distribution wherein the second large size is larger than the first large size, both of which are larger than $S_0$. The very small particles of milled product substrate are all smaller than all of the small size milling media. Another example includes a large size distribution of milling media that is larger than $S_0$, together with a first small size distribution and a second small size distribution wherein the second small size distribution is smaller than the first small size distribution, both of which are smaller than $S_0$. The very small particles of product substrate are all smaller than all of the second smaller size milling media as well as being smaller than all particles of the first small size milling media.

The large media particle size distribution is chosen such that the large particles will form a depth filter on the screen and restricts the small media particles from leaving the milling vessel. As depicted in FIG. 4 which shows a depth filter concept comprising substantially uniform large size spherical bead media, an array comprising one or more layers of large media particles builds up on the surface of the screen proximal to the milling chamber. The build up of particles may be uniform for example comprising substantially uniformly sized spherical milling media beads and void spaces between the beads that form channels around the beads in the depth filter. If the large particles are not substantially uniformly sized spherical particles, the depth filter can comprise a non-uniform array of particles containing irregular size void spaces and channels. Such can be the case when non-spherical milling media such as torroidal or cylindrical milling media are used or when a non-uniformly sized, randomly packed distribution of spherical milling media are used, or when mixtures of spherical and non-spherical milling media are used, and so forth. These layers of large media particles form the depth filter which restricts the small media particles from leaving the milling vessel. The fluid carrier and very small particles of milled product substrate can pass through the channels in the depth filter. Thus, the very small particles must be smaller than those void spaces and channels. As a corollary, the lower limit size of the small milling media particles is such that they will not pass completely through the void spaces and channels in the depth filter.

In the application of this concept to the media milling process, the large media particle size distribution and the volume fraction of large milling media can be optimized relative to the small media particle size distribution and volume fraction by experimentation to achieve a depth filter with void spaces and channels applicable to use with the small media particles to achieve the desired milled substrate particle size in the milling process. For most applications it is desirable to minimize the volume fraction of large particles since a larger volume fraction of small media particles can contribute to faster milling and smaller final product particle sizes. The small media particles are chosen to be a size distribution which is small enough to pass through the screen in the absence of a depth filter comprising large particles but large enough to be filtered by the depth filter comprised of large media particles on the screen. The size of the small media particles can be chosen for example by comparison with a media milling procedure that does not contain large particles to provide an optimum rate of milling and to yield the desired small final product particle size.

Selection of combinations of separator screen opening size $S_0$, small size milling media size $S_2$, and large size milling media size $S_1$ in which the large size media or mixture of large and small size media can form a depth filter having channels (i.e., voids and spaces) comprising a distribution of channel sizes equal to or greater than the size $S_3$ of the very small milled substrate particles produced in this invention but which channels are smaller than $S_2$ can be made by one skilled in the art to achieve passage of fluid carrier and only the very small milled substrate particles of desired size through the depth filter. For example, sizes of milling media and openings can be adjusted to provide passage of only very small particles of size less than 2 micrometers in the fluid carrier; other combinations can provide passage of only very small particles of size less than 1 micrometer in the fluid carrier; still other combinations can provide passage of only very small particles of size less than 0.5 micrometer in the fluid carrier; still other combinations can provide passage of only very small particles of size less than 0.4 micrometer in the fluid carrier; still other combinations can provide passage of only very small particles of size less than 0.3 micrometer in the fluid carrier; still other combinations can provide passage of only very small particles of size less than 0.2 micrometer in the fluid carrier; still other combinations can provide passage of only very small particles of size less than 0.1 micrometer in the fluid carrier; still other combinations can provide passage of only very small particles of size less than 0.05 micrometer in the fluid carrier; and still other combinations can provide passage of only very small particles of size less than 0.01 micrometer in the fluid carrier.

Grinding media suitable for use in this invention can comprise a wide range of known and commercially available milling media. In one embodiment, the large and small media can be preferably substantially spherical in shape such as beads. The media can be made of a number of materials well known in the art including dense and hard materials such as sand, steel, silicon carbide, ceramics, zirconium silicate, zirconium and yttrium oxide, glass, alumina, titanium, certain polymeric resins such as crosslinked polystyrene and methyl methacrylate, and biodegradable polymers. Composites of inorganic media covered with crosslinked organic polymers are also useful. The composition of the large media can be the same or different from the composition of the small media. The composition of the large media can be uniform or can be a mixture of milling media compositions such as steel and zirconium silicate of size distribution $S_1$. The composition of the small media can be uniform or can be a mixture of milling media compositions such as crosslinked polystyrene and zirconium silicate of size distribution $S_2$.

In another embodiment, grinding media in the form of other non-spherical shapes are expected to be useful in the practice of this invention. Such shapes include cylindrical and torroidal shapes. Combinations of grinding media with different shapes are also contemplated to be advantageous. For example, a depth filter of large size grinding media can comprise large torroidal grinding media and large spherical beads or cylinders and be used in conjunction with small sized spherical, cylindrical, cubical, or torroidal shaped grinding media or combinations of small media of different shapes. Preferably, the small media can be spherical and the large media can be spherical or torroidal in shape.

Depending on the relative hardness and toughness of the media and the relative hardness and toughness of the substrate to be milled, the surfaces of the large media can be smooth or they can be roughened or ridged when harder and tougher than the small media and substrate to be milled. In one aspect, use of roughened or ridged large media in the depth filter can provide larger channels and void spaces in the depth filter than when smooth surfaces are used and permit faster flow rates through the depth filter of fluid carrier and dispersion of very small milled product substrate particles.

Grinding media comprising polymeric resins are suitable for use in this invention. Such resins can be chemically and physically inert, substantially free of metals, solvent and monomers, and of sufficient hardness and friability to enable them to avoid being chipped or crushed during grinding. Suitable polymeric resins include crosslinked polystyrenes, such as polystyrene crosslinked with divinylbenzene, styrene copolymers, polyacrylates such as polymethyl methylcrylate, polycarbonates, polyacetals, such as Delrin™, vinyl chloride polymers and copolymers, polyurethanes, polyamides, poly(tetrafluoroethylenes), e.g., Teflon™, and other fluoropolymers, high density polyethylenes, polypropylenes, cellulose ethers and esters such as cellulose acetate, polyhydroxymethacrylate, polyhydroxyethyl acrylate, silicone containing polymers such as polysiloxanes and the like.

In another aspect, the polymeric material of which grinding media are comprised can be biodegradable. Exemplary biodegradable polymers include poly(lactides), poly (glycolide) copolymers of lactides and glycolide, polyanhydrides, poly(hydroxyethyl methacrylate), poly (imino carbonates), poly(N-acylhydroxyproline)esters, poly (N-palmitoyl hydroxyproline) esters, ethylene-vinyl acetate copolymers, poly(orthoesters), poly(caprolactones), and poly(phosphazenes). In the case of biodegradable polymers, contamination from the media itself advantageously can metabolize in vivo into biologically acceptable products which can be eliminated from the body.

Polymeric resin can have a density from 0.8 to about 3 g/cm$^3$. Higher density resins are preferred because they can provide more efficient particle size reduction. The use of polymeric resins also enable improved pH control.

Various inorganic grinding media prepared in the appropriate particle size are suitable for use in this invention. Such media include zirconium oxide, such as 95% ZrO stabilized with magnesia, zirconium silicate, glass, stainless steel, titania, alumina, and 95% ZrO stabilized with yttrium.

In one aspect, small media of this invention can range in size up to about 1000 micrometers. However, it is particularly advantageous that the invention enables the use of grinding media having a particle size of less than about 350 micrometers. More preferably, the media is less than about 100 micrometers, and, most preferably, less than about 75 micrometers, in size.

The small grinding media can comprise particles, preferably substantially spherical in shape, e.g., beads, consisting essentially of a polymeric resin. Alternatively, the small grinding media can comprise particles comprising a core having a coating of a polymeric resin adhered thereon.

Media compositions may include glass, ceramics, plastics, steels, etc. In a preferred embodiment, the milling media material can comprise particles, preferably substantially spherical in shape, e.g., beads, consisting essentially of a polymeric resin. Polymeric media can be preferred due to low density and good chemical and physical stability.

A preferred method of making polymeric beads and torroidal grinding media especially large size torroidal grinding media is by polymerization of acrylic and vinylbenzene monomers such as styrene, divinylbenzene, and trivinyl benzene. Methyl methacrylate and styrene are preferred monomers because they are inexpensive, commercially available materials which make acceptable polymeric grinding media. Other acrylic and styrenic monomers have also been demonstrated to work in grinding media. Styrene is preferred. However, free radical addition polymerization in general, and suspension polymerization in particular, can not be carried to 100% completion. Residual monomers can remain in the beads and torroids and can leach out during the milling process and contaminate the product dispersion unless removed.

Removal of the residual monomers can be accomplished by any number of methods common to polymer synthesis such as thermal drying, stripping by inert gases such as air or nitrogen, solvent extraction or the like. Drying and stripping processes are limited by low vapor pressure of residual monomers and large bead sizes resulting in long diffusion paths. Solvent extraction is therefore preferred. Useful solvents include acetone, toluene, alcohols such as methanol, alkanes such as hexane, supercritical carbon dioxide and the like. Acetone is preferred for crosslinked styrene beads. Solvents which are effective in removing residual monomers typically dissolve non-crosslinked polymer made from the monomer or otherwise make the polymer sticky and difficult to handle. Therefore, it is preferred to crosslink the polymer to make it insoluble in the solvent which has an affinity for the monomer. Methods of crosslinking of polymers are well known to those skilled in the art and includes use of multifunctional monomers in radical polymerization, use of di- and tri-functional crosslinking agents that can react with a functional group on a polymer after polymerization, ultraviolet and other light sensitive agents that can react photochemically, vulcanizing agents, hardeners, and the like.

Enough crosslinker to make the polymer insoluble, typically a few percent, is required but any amount can be used as long as the bead performs adequately as a grinding media. Pure commercially available divinylbenzene (usually containing about 55% divinylbenzene) is known to make beads which break up and contaminate the product in a milling process. Any monomer with more than one ethylenically unsaturated group can be used such as divinylbenzene and ethylene glycol dimethacrylate. Divinylbenzene is preferred and a copolymer of 20% styrene, 80% commercial divinylbenzene (55% assay) is especially preferred.

To make spherical beads, suspension polymerization is preferred. To make large torroidal grinding media, large bead particles can be individually milled or drilled into the shape of a torroid. Alternatively, a liner rod of a polymer that is a solid at milling use temperatures and prepared by extrusion of a bulk polymer through an orifice or hole in a die can be softened by heating and looped into the form or a torroid and then cooled. Optionally, the polymer in the loop can contain crosslinkable sites such as residual olefinic sites that can be irradiated with light to further crosslink and harden the large torroidal or bead milling media. Additionally, the torroid can be swollen with a crosslinkable monomer such as divinylbenzene and trivinylbenzene and then irradiated or heated to activate a crosslinking reaction that will essentially fix the shape of the torroid and prevent it from changing shape substantially for that of a torroid.

Another method useful to produce torroidal milling media is to thermally extrude a heated polymer such as polystyrene from a die to form an extruded polymer in the form of a tube and then cut or slice the tube into torroid shapes that can be cooled to provide torroidal milling media. These polystyrene tubes can then be further treated with for example additional monomers such as styrene and crosslinking monomers that can coat the surfaces of the torroid and then be polymerized and crosslinked to provide torroids that are suitable for use as milling media.

The size of the torroid can depend on the method of its production. For example, if derived from a polymer in the form of a tube that is sliced into torroids, the thickness of the tube wall, the width of the slice of the tube and the external and internal diameters dictate the dimensions of the torroid. Tubing with an external diameter that is from 1.1 to about 100 times the internal diameter can be used to produce torroids. Slice thickness can be from 0.1 to about 20 times the external diameter of the tube to form a useful torroid. Tubing cut larger than about 20 times the external diameter can be used, but such shapes can then be called hollow cylinders. These shapes will also be useful as milling media in this invention.

Optionally, the tubing can be unsymmetrically stretched or distorted to form other than a right circular torroid or cylindrical shape for example by heating to soften the torroid and then pulling in the walls of the torroid in two opposite directions to provide an oval distortion. The distorted torrid can then be cooled and further crosslinked as above to provide large size grinding media useful in this invention.

The invention can be practiced in conjunction with various inorganic milling media prepared in the appropriate particle size. Such media include zirconium oxide, such as 95% zirconium oxide stabilized with magnesia, zirconium silicate, glass, stainless steel, titania, alumina, and 95% zirconium oxide stabilized with yttrium. Inorganic milling media can serve as core material and formed into shapes such as spheres and torroids and can be coated with polymer such as crosslinked polystyrene or crosslinked polymethylmethacrylate.

The core material preferably can be selected from materials known to be useful as grinding media when fabricated as spheres or particles. Suitable core materials include zirconium oxides (such as 95% zirconium oxide stabilized with magnesia or yttrium), zirconium silicate, glass, stainless steel, titania, alumina, ferrite and the like. Preferred core materials have a density greater than about 2.5 g/cm$^3$. The selection of high density core materials is believed to facilitate efficient particle size reduction.

Useful thicknesses of the polymer coating on the core are believed to range from about 1 to about 500 micrometers, although other thicknesses outside this range may be useful in some applications. The thickness of the polymer coating preferably is less than the diameter of the core.

The cores can be coated with the polymeric resin by techniques known in the art. Suitable techniques include spray coating, fluidized bed coating, and melt coating. Adhesion promoting or tie layers can optionally be provided to improve the adhesion between the core material and the resin coating. The adhesion of the polymer coating to the core material can be enhanced by treating the core material to adhesion promoting procedures such as roughening of the core surface, corona discharge treatment, and the like.

Small particles can be prepared by known methods including suspension bead polymerization, latex polymerization, swelling of latex polymer particles with additional styrene or methacrylate monomers optionally including crosslinking monomers followed by polymerization, spray drying of solutions of polymers optionally followed by crosslinking, and other known methods used to prepare small particle milling media. Small particle milling media can also comprise inorganic materials in their entirety or in part, the latter also comprising coatings of organic polymer prepared according to well known methods. Small milling media are preferably spherical or bead shaped media.

The milling process can be a dry milling process wherein the fluid carrier is a gas including inert or non-reactive gases and reactive gases. Reactive gases will react with ions or radicals formed in the milling of substrates. Reactive gases include oxygen as an oxidizing gas, air which contains oxygen, air enriched with additional oxygen, hydrogen as a reducing gas, olefinic and unsaturated gases such as ethylene and propylene, and carbon dioxide which can react in water to form carbonic acid and with base to form bicarbonate and carbonate, a chlorofluorocarbon gas such as chlorotrifluoromethane which can react to transfer chlorine to the substrate, and dimethyl ether which can react to transfer hydrogen to the substrate. Preferred reactive gases as fluid carriers include air and carbon dioxide. Non-reactive gases are gases that will not readily react as oxidizing or reducing agents in the presence of ions or radicals formed in the milling of substrates. Non-reactive gases include air depleted of oxygen, nitrogen, argon which is an inert gas (as are helium and neon), a fluorocarbon gas such as perfluorpropane, a saturated hydrocarbon gas such as propane, and mixtures of these gases. Preferred non-reactive gases are nitrogen and air depleted of oxygen. A preferred inert gas is argon.

In one aspect, the fluid carrier can be selected from the group consisting of a gas as described herein, a liquefied compressed gas such a liquified propane or butane, a supercritical fluid such as supercritical carbon dioxide, supercritical ethane, supercritical propane, supercritical dimethyl ether, a supercritical fluid containing one or more dissolved excipients as described herein, and a supercritical fluid containing one or more surface active agents as described herein. When these gases or liquified gases or supercritical fluids are used, the media mill must be configured to contain the gases or pressurized gases or fluids.

In another aspect, the fluid carrier can be a compressed or pressurized gas such as compressed nitrogen or argon, or the fluid carrier can be a gas maintained under pressure in the form of a supercritical fluid. Examples of supercritical fluids include supercritical carbon dioxide, supercritical dimethyl ether, supercritical hydrocarbons such as supercritical methane, supercritical ethane, and supercritical propane and mixtures of supercritical fluids. The fluid carrier can also comprise a supercritical fluid containing one or more dissolved materials such as one or more excipients, one or more surface active agents, and the like. The fluid carrier can also comprise a solution of a solvent in a supercritical fluid or a solution of a supercritical fluid in a solvent. Solutions of such materials and solutions of mixtures of such materials can range from about 0.01% by weight of fluid up to the saturation point of the solubility of the materials in a supercritical fluid being employed according to this invention. Preferred concentrations of surface active agent material in a supercritical fluid range from about 0.01% up to about 10% when such solubilities can be achieved.

The milling process can be a wet milling process, also sometimes referred to as a wet-grinding process, wherein the fluid carrier is a liquid. Useful liquid fluid carriers include water, sterile water, water for injection, aqueous salt solutions such as PBS, aqueous phosphate buffered saline, buffered aqueous solutions, sugar-containing water, an aqueous solution comprising from 1% to 25% (and up to saturation levels) of a carbohydrate, an aqueous solution of a surface active substance, an aqueous solution of a surface active substance mixed with undissolved surface active substance, ethanol, methanol, butanol, hexane, hydrocarbons, kerosine, PEG-containing water, glycol, toluene, glyme, petroleum-based solvents, ligroin, mixtures of aromatic solvents such as xylenes and toluene, heptane, mixtures of water miscible solvents and water, DMSO, DMF, and the like. In one aspect where pharmaceutical agents are substrates in the invention, preferred liquid fluid carriers include water, sterile water, water for injection, aqueous salt solutions of one or more salts such as PBS, solutions of aqueous buffers, aqueous phosphate buffered saline, sugar-containing water, aqueous solutions of one or more pharmaceutical excipients, aqueous solution comprising from about 1% to about 25% (and up to saturation levels) of a carbohydrate, aqueous solutions of one or more surface active substances mixed with one or more undissolved liquid surface active substances, PEG-containing water, ethanol, and mixtures of these liquid carriers.

Wet grinding can be accomplished in conjunction with a liquid carrier fluid and one or more than one surface active substance especially when the very small particles are less than about 10 microns. These carrier fluids can also contain dissolved materials such as pharmaceutical excipients such as carbohydrates. Useful liquid fluid carriers include water, aqueous salt and/or buffer solutions, ethanol, butanol, hexane, glycol and the like. The surface active substance can be selected from known organic and inorganic pharmaceutical excipients that have surface modifying properties and can be present in an amount of 0.1–90%, preferably 1–80% by weight based on the total weight of the dry substrate. Preferred surface active substances are phospholipids.

The conglomerate of solid substrate used in this invention can comprise any crystalline or amorphous solid material that can be milled in a media mill. The conglomerate generally consists of a solid substrate to be milled in the form of a powder, glass, a distribution of particles that can range in size from $S_2$ to the size of the entry port in the media mill. With respect to the milling process of this invention, the conglomerate is generally a solid that may be a single crystalline form, a mixture of crystalline forms, an amorphous solid, or a mixture of solids to be milled. The size of at least some of the components of the solid is generally larger than the size of very small particles produced in this invention, although the conglomerate may contain a range of sizes including some very small particles that can form a dispersion in the fluid carrier and pass through the depth filter. Such particles are, however, generally produced in the process of the invention by media milling and size reduction of the solid substrate in the conglomerate. The solid substrate may be in the form of any shape that is suitable for milling and size reduction to form very small particles. The conglomerate may contain a precipitated solid, a recrystalized solid, a partially milled solid such as a previously media milled solid, a jet milled solid, a partially ground solid, a micronized solid, a pulverized solid, a ball milled solid, a triturated solid, a sublimed solid, a residue from an evaporation, a solid derived from a synthetic process, a solid derived from an extract such as an organic solvent extraction or supercritical fluid extraction from a mixture such as reaction product or plant or tissue extract. The solid is preferably poorly water-soluble or essentially water-insoluble.

Examples of solid material that can be milled according to the methods of this invention include solid pigments; solid photographic materials such as dyes; solid cosmetic ingredients; solid chemicals; solid metal powders; solid catalyst materials; solid support material for catalysts; solid stationary phase particles or support materials useful in analytical and preparative chromatography; solid toner materials such as black toner materials and colored toner materials that are useful in xerographic and printing applications including laser printing; and solid pharmaceutical agents including water-soluble, water-insoluble, essentially water-insoluble and poorly water-soluble therapeutic and diagnostic imaging agents, medicinally active agents, medicaments, plant and herbal extracts, drugs, pro-drugs, drug formulations, diagnostic imaging agents, and the like. Preferred solid materials are pharmaceutical agents, and most preferred are poorly water-soluble, water-insoluble and essentially water-insoluble pharmaceutical agents.

The conglomerate of solid substrate can optionally comprise a surface active substance. Surface active substances are known to provide stability to small particles prepared in milling and other size reduction processes.

In a preferred aspect, the substrate in the starting agglomerate can comprise a pharmaceutical substance such as a therapeutic or diagnostic agent. When the substrate is ground or reduced in size sufficiently to pass through the depth filter, the product substrate particles can be continuously removed from the milling chamber by passage through the depth filter wherein the small and large milling media are retained together with unmilled or partially milled substrate that is too large to pass through the depth filter. Product substrate particles are not retained while media and unmilled or partially milled substrate particles are restricted from leaving the milling chamber of the media mill.

The invention can be practiced with a wide variety of substrates including therapeutic and diagnostic agents. In the case of dry milling where the fluid carrier is a gas, the substrates must be capable of being formed into solid particles. In the case of wet milling where the fluid carrier is a liquid, the substrates must be poorly soluble and dispersible in at least one liquid medium. By "poorly soluble" it is meant that the substrate has a solubility in the liquid dispersion medium, e.g., water, of less than about 10 mg/ml, and preferably of less than about 1 mg/ml. A preferred liquid dispersion medium or fluid carrier is water and solutions in water such as salt solutions and optionally containing buffering agents such as phosphate buffer and optionally containing carbohydrates and/or surface active agents. Additionally, the invention can be practiced with other liquid media. The substrates can be organic solids, either crystalline or amorphous materials, or they may be inorganic solids as long as they can be reduced in size by the milling process. Organic solids can be single compounds or mixtures of compounds, enantiomers, optical isomers, racemic mixtures, diastereomers, isomers, blends, glasses, separate crystal forms of a single substance, eutectic mixtures, or formulations of different compounds such as a drug substance and a surface active substance.

Suitable diagnostic imaging agents include X-ray contrast agents and magnetic resonance imaging (MRI) contrast agents. Useful X-ray contrast agents are, for example, iodinated aromatic acid derivatives such as ethyl-3,5-bisacetoamido-2,4,6-triiodobenzoate, ethyl(3,5-bis(acetylamino)-2,4,6-triodobenzoyloxy) acetate, ethyl-2-(bis(acetylamino)-2,4,6-triodobenzoyloxy)butyrate, 6-ethoxy-6-oxohexyl-3,5-bis(acetylamino)-2,4,6-triiodobenzoate. Useful MRI contrast agents include iron oxide particles.

In one embodiment, milled substrates can be prepared in submicrometer or nanoparticulate particle size, e.g., less than about 500 nm. Particles having an average particle size of less than 100 nm can be prepared in accordance with the present invention and usually require the presence of surface active agent to stabilize the particles against growth by Ostwald ripening or against agglomeration and/or aggregation.

In preferred embodiments, very small particles of a therapeutic or diagnostic agent can be prepared in submicrometer or nanoparticulate particle size, e.g., less than about 500 nm. Particles can be prepared having an average particle size of less than about 300 nm. In certain embodiments, particles having an average particle size of less than 100 nm can be prepared in accordance with the present invention. Surface active agents are needed to stabilize these particles against growth.

Preferred proportions of the grinding media, substrate such as a therapeutic or diagnostic agent, fluid carrier, and surface active substance present in the milling chamber of a media mill can vary within wide limits and depend, for example, upon the particular substrate such as the kind of therapeutic or diagnostic agent selected, and the sizes and densities of the grinding media. Total grinding media concentrations can range from about 10–95%, preferably 20–90% by volume depending on the application and can be optimized based on the above factors, milling performance requirements, and the flow characteristics of the combined grinding media and substrate dispersion. In high energy media mills, it can be desirable to fill 70–90% of the volume of the grinding chamber with grinding media.

The attrition time can vary widely and depends primarily upon the particular substrate such as a therapeutic or diagnostic agent to be milled, energy transfer efficiency in the media mill, and mill residence conditions selected, the initial and desired final particle size, relative media size distributions, and so forth. Residence times of less than about ten hours are often required using high energy media mills.

The process can be carried out within a wide range of temperatures and pressures. The process preferably is carried out at a temperature below that which can cause the substrate to degrade or which can cause the surface active agent, if present, to degrade. For many substrates, ambient temperatures are appropriate. Temperatures of less than about 30° C. to 40° C. are typically preferred. The temperature of the media mill is maintained below the melting point of the solid substrate being milled during the process of this invention. Control of the temperature, e.g., by jacketing or immersion of the milling chamber in cold water, ice water, a heated or cooled air bath, and by electical resistance heating are contemplated. Processing pressures from about 1 psi up to about 50 psi are contemplated. Processing pressures from about 10 psi to about 30 psi are typical.

In a preferred embodiment, particles of the substrate that are ground small enough to pass through the depth filter can be recirculated through the milling chamber. Examples of suitable means to effect such recirculation include conventional pumps such as peristaltic pumps, diaphragm pumps, piston pumps, centrifugal pumps and other positive displacement pumps. Peristaltic pumps are generally preferred. Optionally, during the recirculation of the fluid carrier dispersion of the product substrate particles, the product substrate particles or a portion of the product substrate particles can be isolated or the dispersion can be concentrated to provide the product particles for isolation as desired.

Milling can take place in the milling chamber of a suitable media milling apparatus. Suitable media mills are those in which a depth filter can be formed from large size milling media or from a mixture of large and small size milling media. Suitable mills include high energy media mills which are preferred when the grinding media is a polymeric resin. The media mill can contain a rotating shaft. The invention can also be practiced in conjunction with high speed dispersers such as a Cowles disperser, rotor-stator mixers, or other conventional mixers which can deliver high fluid carrier velocity and high shear and which contain a suitable separator or screen on which a depth filter can be formed from large size milling media according to this invention.

Preferred vessel geometries include diameter to depth ratios of about 1:1 to 1:10. Vessel volumes may range from less than 1 cc to over 4000 liters. A vessel cover may be used to prevent contamination in the milling chamber and/or allow for pressurization or vacuum. It is preferred that jacketed vessels be used to allow temperature control during milling. Processing temperatures may span the range between the freezing and boiling temperatures of the liquid vehicle used to suspend the particles. Higher pressures may be used to prevent boiling. Common agitator designs may include axial or radial flow impellers, pegs, discs, high-speed dispersers, etc. Mixers employing radial flow are preferred since the provide high media velocity and shear with minimal pumping action which may be detrimental to milling performance. Mixer tip speeds of 1 to 50 m/sec may be used, although speeds of 10 to 40 m/sec are preferred in simple vessel designs. Milling times may range from about 1 hour to 100 hours or more in such high speed mixing mills, depending on desired particle size, formulations, equipment and processing conditions.

The preferred proportions of the milling media, the substrate to be milled, the liquid dispersion medium and any surface active substance can vary within wide limits and can depend, for example, upon the particular substrate material selected, the relative size and density and hardness and toughness of the small and large milling media, the operating speed of the mill selected, etc. Preferred milling media concentrations depend upon the application and can be optimized based on milling performance requirements, and the flow characteristics of the substrate to be milled. Preferably, between approximately 30 to 100 percent of the slurry of the substrate to be milled resides in the interstitial voids between adjacent small media beads. Where the void volume of randomly-packed spheres is approximated to be about 40 percent, the corresponding preferred volume ratio of small milling media to slurry of substrate to be milled in the milling vessel ranges from 0.5 to 1.6. It is preferred that between 60 to 90 percent of slurry reside in small media voids to maximize milling efficiency. The uniformity of the voids is, of course, distorted by the presence of large milling media in the milling chamber in addition to in the depth filter.

In a preferred aspect, the present invention relates to an improved process for the preparation of very small particles containing a poorly water-soluble drug, and in particular to an improved process for the preparation of very small particles containing a poorly water-soluble drug as a dispersion in an aqueous carrier and as dried small particles containing a poorly water-soluble drug. The very small particles are preferably stabilized by a surface active agent that is present during the size reduction milling process of this invention.

As used herein, "very small particle" refers to a particle or a distribution of particles having a diameter or an average diameter, respectively, of from nanometers to micrometers. Very small particles are microparticles and nanoparticles, as used herein, and also refer to solid particles of irregular, non-spherical or spherical shapes.

Formulations containing these small particles or microparticles provide some specific advantages over unformulated non-milled drug particles. These advantages include improved oral bioavailability of drugs that are poorly absorbed from the GI tract, development of injectable formulations that are currently available only in oral dosage form, less toxic injectable formulations that are currently prepared with organic solvents, sustained release of intramuscular injectable drugs that are currently administered through daily injection or constant infusion, and preparation of inhaled and ophthalmic formulations of drugs that otherwise could not be formulated for nasal or ocular use.

Water-insoluble, essentially water-insoluble, and poorly water-soluble compounds are those having poor solubility in water at or below normal physiological temperatures, that is <5 mg/ml at physiological pH (6.5–7.4). Preferably their water solubility is <1 mg/ml, and more preferably <0.1 mg/ml. It is desirable that the drug be stable in water as a dispersion. Otherwise or in addition a dried form such as a lyophilized or spray-dried solid form may be desirable for example for use in formation of drug delivery compositions including capsules, tablets, and formulations with additional excipients and drugs.

Examples of some preferred water-insoluble drugs include immunosuppressive and immunoactive agents, antiviral and antifungal agents, antineoplastic agents, analgesic and anti-inflammatory agents, antibiotics, anti-epileptics, anesthetics, hypnotics, sedatives, antipsychotic agents, neuroleptic agents, antidepressants, anxiolytics, anticonvulsant agents, antagonists, neuron blocking agents, anticholinergic and cholinomimetic agents, antimuscarinic and muscarinic agents, antiadrenergic and antarrhythmics, antihypertensive agents, antineoplastic agents, hormones, and nutrients. A detailed description of these and other suitable drugs may be found in Remington's Pharmaceutical Sciences, 18th edition, 1990, Mack Publishing Co. Philadelphia, Pa. which is hereby incorporated by reference.

Suitable compounds can have pharmaceutical efficacy in a number of therapeutic and diagnostic imaging areas. Non-limiting classes of compounds and agents from which poorly water-soluble drugs such as those that melt or fracture without decomposition and are useful in this invention can be selected include anesthetic agents, ace inhibiting agents, antithrombotic agents, anti-allergic agents, antibacterial agents, antibiotic agents, anticoagulant agents, anticancer agents, antidiabetic agents, antihypertension agents, antifungal agents, antihypotensive agents, antiinflammatory agents, antimicotic agents, antimigraine agents, antiparkinson agents, antirheumatic agents, antithrombins, antiviral agents, beta blocking agents, bronchospamolytic agents, calcium antagonists, cardiovascular agents, cardiac glycosidic agents, carotenoids, cephalosporins, contraceptive agents, cytostatic agents, diuretic agents, enkephalins, fibrinolytic agents, growth hormones, immunosurpressants, insulins, interferons, lactation inhibiting agents, lipid-lowering agents, lymphokines, neurologic agents, prostacyclins, prostaglandins, psycho-pharmaceutical agents, protease inhibitors, magnetic resonance diagnostic imaging agents, reproductive control hormones, sedative agents, sex hormones, somatostatins, steroid hormonal agents, vaccines, vasodilating agents, and vitamins.

Non-limiting examples of representative poorly soluble drugs useful in this invention include albendazole (m.p. 208–210° C.), albendazole sulfoxide, alfaxalone (m.p. 172–174° C.), acetyl digoxin, acyclovir analogs melting at or below 275° C., alprostadil, aminofostin, anipamil, antithrombin III, atenolol (m.p. 146–148° C.), azidothymidine, beclobrate (m.p. 200–204° C.), beclomethasone (m.p. 117–120° C.), belomycin, benzocaine (m.p. 88–90° C.) and derivatives, beta carotene (m.p. 183° C.), beta endorphin, beta interferon, bezafibrate (m.p. 186° C.), binovum, biperiden (m.p. 112–116° C.), bromazepam (m.p. 237–238° C.), bromocryptine, bucindolol, buflomedil (m.p. 192–193° C.), bupivacaine (m.p. 107–108° C.), busulfan (m.p. 114–118° C.), cadralazine (m.p. 160–162° C.), camptothesin (m.p. 264–267 and 275° C.), canthaxanthin (m.p. 217° C.), captopril (m.p. 103–104° C.), carbamazepine (m.p. 190–193° C.), carboprost, cefalexin, cefalotin, cefamandole (m.p. 190° C.), cefazedone, cefluoroxime, cefmenoxime, cefoperazone (m.p. 169–171° C.), cefotaxime, cefoxitin (m.p. 149–150° C.), cefsulodin (m.p. 175° C.), ceftizoxime, chlorambucil (m.p. 64–66° C.), chromoglycinic acid, ciclonicate (m.p. 127–128° C.), ciglitazone, clonidine (m.p. 130° C.), cortexolone, corticosterone (m.p. 180–182° C.), cortisol (m.p. 212–220° C.), cortisone (m.p. 220–22° C.), cyclophosphamide (m.p. 41–45° C.), cyclosporin A (m.p. 148–151° C.) and other cyclosporins, cytarabine (m.p. 212–213° C.), desocryptin, desogestrel (m.p. 109–110° C.), dexamethasone esters such as the acetate (m.p. 238–240° C.), dezocine, diazepam (m.p. 125–126° C.), diclofenac, dideoxyadenosine (m.p. 160–163° C.), dideoxyinosine, digitoxin (m.p. 256–257° C.), digoxin, dihydroergotamine (m.p. 239° C.), dihydroergotoxin, diltiazem (m.p. 207–212° C.), dopamine antagonists, doxorubicin (m.p. 229–231° C.), enconazole (m.p. 87° C.), endralazine (m.p. 185–188° C.), enkephalin, enalapril (m.p. 143–145° C.), epoprostenol, estradiol (m.p. 173–179° C.), estramustine (m.p. 104–105° C.), etofibrate (m.p. 100° C.), etoposide (m.p. 236–251° C.), factor ix, factor viii, felbamate (m.p. 151–152° C.), fenbendazole (m.p. 233° C.), fenofibrate (m.p. 79–82° C.), flunarizin (m.p. 252° C.), flurbiprofen (m.p. 110–111° C.), 5-fluorouracil (m.p. 282–283° C.), flurazepam (m.p. 77–82° C.), fosfomycin (m.p. ~94° C.), fosmidomycin, furosemide (m.p. 206° C.), gallopamil, gamma interferon, gentamicin (m.p. 102–108° C.), gepefrine (m.p. 155–158° C.), gliclazide (m.p. 180–182° C.), glipizide (m.p. 208–209° C.), griseofulvin (m.p. 220° C.), haptoglobulin, hepatitis B vaccine, hydralazine (m.p. 172–173° C.), hydrochlorothiazide (m.p. 273–275° C.), hydrocortisone (m.p. 212–220° C.), ibuprofen (m.p. 75–77° C.), ibuproxam (m.p. 119–121° C.), indinavir, indomethacin (m.p. 155° C.), iodinated aromatic x-ray contrast agents melting below 275° C. such as iodamide (m.p. 255–257° C.), ipratropium bromide (m.p. 230–232° C.), ketoconazole (m.p. 146° C.), ketoprofen (m.p. 94° C.), ketotifen (m.p. 152–153° C.), ketotifen fumarate (m.p. 192° C.), K-strophanthin (m.p. ~175° C.), labetalol, lactobacillus vaccine, lidocaine (m.p. 68–69° C.), lidoflazin (m.p. 159–161° C.), lisuride (m.p. 186° C.), lisuride hydrogen maleate (m.p. 200° C.), lorazepam (m.p. 166–168° C.), lovastatin, mefenamic acid (m.p. 230–231° C.), melphalan (m.p. 182–183° C.), memantin, mesulergin, metergoline (m.p. 146–149° C.), methotrexate (m.p. 185–204° C.), methyl digoxin (m.p. 227–231° C.), methylprednisolone (m.p. 228–237° C.), metronidazole (m.p. 158–160° C.), metisoprenol, metipranolol (m.p. 105–107° C.), metkephamide, metolazone (m.p. 253–259° C.), metoprolol, metoprolol tartrate, miconazole (m.p. 135° C.), miconazole nitrate (m.p. 170 and 185° C.), minoxidil (m.p. 248° C.), misonidazol, molsidomin, nadolol (m.p. 124–136° C.), nafiverine (m.p. 220–221° C.), nafazatrom, naproxen (m.p. 155° C.), natural insulins, nesapidil, nicardipine (m.p. 168–170° C.), nicorandil (m.p. 92–93° C.), nifedipine (m.p. 172–174° C.), niludipin, nimodipine, nitrazepam (m.p. 224–226° C.), nitrendipine, nitrocamptothesin, 9-nitrocamptothesin, oxazepam (m.p. 205–206° C.), oxprenolol (m.p. 78–80° C.), oxytetracycline (m.p. 181–182° C.), penicillins such as penicillin G benethamine (m.p. 147–147° C.), penecillin 0 (m.p. 79–81° C.), phenylbutazone (m.p. 105° C.), picotamide, pindolol (m.p. 171–173° C.), piposulfan (m.p. 175–177° C.), piretanide (m.p. 225–227° C.), piribedil (m.p. 98° C.), piroxicam (m.p. 198–200° C.), pirprofen (m.p. 98–100° C.), plasminogenic activator, prednisolone (m.p. 240–241° C.), prednisone (m.p. 233–235° C.), pregnenolone (m.p. 193° C.), procarbacin, procaterol, progesterone (m.p. 121° C.), proinsulin, propafenone, propanolol, propentofyllin, propranolol (m.p. 96° C.), rifapentin, simvastatin, semi-synthetic insulins, sobrerol (m.p. 130° C.), somastotine and its derivatives, somatropin, stilamine, sulfinalol whose hydrochloride melts at 175° C., sulfinpyrazone (m.p. 136–137° C.), suloctidil (m.p. 62–63° C.), suprofen (m.p. 124° C.), sulproston, synthetic insulins, talinolol (m.p. 142–144° C.), taxol, taxotere, testosterone (m.p. 155° C.), testosterone propionate (m.p. 118–122° C.), testosterone undecanoate, tetracane HI (m.p. ~150° C.), tiaramide (HCl m.p. 159–161° C.), tolmetin (m.p. 155–157° C.), tranilast (m.p. 211–213° C.), triquilar, tromantadine (HCl m.p. 157–158° C.), urokinase, valium (m.p. 125–126° C.), verapamil (m.p. 243–246° C.), vidarabine, vidarabine phosphate sodium salt, vinblastine (m.p. 211–216° C.), vinburin, vincamine (m.p. 232–233° C.), vincristine (m.p. 218–220° C.), vindesine (m.p. 230–232° C.), vinpocetine (m.p. 147–153° C.), vitamin A (m.p. 62–64° C.), vitamin E succinate (m.p. 76–78° C.), and x-ray contrast agents such as iodine-containing aromatic derivatives. Drugs can be neutral species or basic or acidic as well as salts such as exist in the presence of an aqueous buffer.

Non-limiting examples of representative poorly soluble drugs useful in this invention also include acyclovir, alprazolam, altretamine, amiloride, amiodarone, benztropine mesylate, bupropion, cabergoline, candesartan, cerivastatin, chlorpromazine, ciprofloxacin, cisapride, clarithromycin, clonidine, clopidogrel, cyclobenzaprine, cyproheptadine, delavirdine, desmopressin, diltiazem, dipyridamole, dolasetron, enalapril maleate, enalaprilat, famotidine, felodipine, furazolidone, glipizide, irbesartan, ketoconazole, lansoprazole, loratadine, loxapine, mebendazole, mercaptopurine, milrinone lactate, minocycline, mitoxantrone, nelfinavir mesylate, nimodipine, norfloxacin, olanzapine, omeprazole, penciclovir, pimozide, tacolimus, quazepam, raloxifene, rifabutin, rifampin, risperidone, rizatriptan, saquinavir, sertraline, sildenafil, acetyl-sulfisoxazole, temazepam, thiabendazole, thioguanine, trandolapril, triamterene, trimetrexate, troglitazone, trovafloxacin, verapamil, vinblastine sulfate, mycophenolate, atovaquone, atovaquone, proguanil, ceftazidime, cefuroxime, etoposide, terbinafine, thalidomide, fluconazole, amsacrine, dacarbazine, teniposide, and acetylsalicylate.

Examples of some suitable surface active substances that are useful in this invention include: (a) natural surfactants such as casein, gelatin, tragacanth, waxes, enteric resins, paraffin, acacia, gelatin, cholesterol esters and triglycerides, (b) nonionic surfactants such as polyoxyethylene fatty alcohol ethers, sorbitan fatty acid esters, polyoxyethylene fatty acid esters, sorbitan esters, glycerol monostearate, polyethylene glycols, cetyl alcohol, cetostearyl alcohol, stearyl alcohol, poloxamers, polaxamines, methylcellulose, hydroxycellulose, hydroxy propylcellulose, hydroxy propylmethylcellulose, noncrystalline cellulose, polyvinyl alcohol, polyvinylpyrrolidone, and synthetic phospholipids, (c) anionic surfactants such as potassium laurate, triethanolamine stearate, sodium lauryl sulfate, alkyl polyoxyethylene sulfates, sodium alginate, dioctyl sodium sulfosuccinate, negatively charged phospholipids (phosphatidyl glycerol, phosphatidyl inosite, phosphatidylserine, phosphatidic acid and their salts), and negatively charged glyceryl esters, sodium carboxymethylcellulose, and calcium carboxymethylcellulose, (d) cationic surfactants such as quaternary ammonium compounds, benzalkonium chloride, cetyltrimethylammonium bromide, chitosans and lauryldimethylbenzylammonium chloride, (e) colloidal clays such as bentonite and veegum. A detailed description of these surfactants may be found in Remington's Pharmaceutical Sciences, and Theory and Practice of Industrial Pharmacy, Lachman et al, 1986.

More specifically, examples of suitable surface active substances include one or combinations of the following: polaxomers, such as Pluronic™ F68, F108 and F127, which are block copolymers of ethylene oxide and propylene oxide available from BASF, and poloxamines, such as Tetronic™ 908 (T908), which is a tetrafunctional block copolymer derived from sequential addition of ethylene oxide and propylene oxide to ethylene-diamine and available from BASF, Triton™ X-200, which is an alkyl aryl polyether sulfonate and available from Rohm and Haas. Tween 20, 40, 60 and 80, which are polyoxyethylene sorbitan fatty acid esters and available from ICI Speciality Chemicals, Carbowax™ 3550 and 934, which are polyethylene glycols available from Union Carbide, hydroxypropylmethylcellulose, dimyristoyl phosphatidylglycerol sodium salt, sodium dodecylsulfate, sodium deoxycholate, and cetyltrimethylammonium bromide.

Preferred surface active substances are phospholipid surface active substances and mixtures comprising phospholipid surface active substances. Suitable phospholipids include animal and plant phospholipids; egg phospholipids; soya bean phospholipids; corn phospholipids; wheat germ, flax, cotton, and sunflower seed phospholipids; milk fat phospholipids; glycerophospholipids; sphingophospholipids; phosphatides; phospholipids containing fatty acid esters including palmitate, stearate, oleate, linoleate, and arachidonate which esters can be mixtures and mixtures of isomers in the phospholipids; phospholipids composed of fatty acids containing one or more than one double bonds such as dioleoyl phosphatidylcholine and egg phosphatidylcholine that are not stable as powders in moist air but are hygroscopic and can absorb moisture and become gummy; phospholipids composed of saturated fatty acids that are stable as powders in moist air and are less amenable to absorption of moisture; phosphatidylserines; phosphatidylcholines; phosphatidylethanolamines; phosphatidylinositols; phosphatidylglycerols such as dimyristoyl phosphatidylglycerol, L-alpha-dimyristoyl phosphatidylglycerol also known as 1,2-dimyristoyl-sn-glycero-3-phospho(rac-1-glycerol) and also known as DMPG; phosphatidic acid; hydrogenated natural phospholipids; and commercially available phospholipids such as those available from Avanti Polar Lipids, Inc. of Alabaster, Ala., USA and other manufacturers. In the absence of an internal counterion in the phospholipid, a preferred counterion is a monovalent cation such as sodium ion. The phospholipid may be salted or desalted, hydrogenated, partially hydrogenated, or unsaturated, natural, synthetic, or semisynthetic.

Preferred phospholipids include Lipoid E80, Lipoid EPC, Lipoid SPC, DMPG, Phospholipon 100H a hydrogenated soybean phosphatidylcholine, Phospholipon 90H, Lipoid SPC-3, and mixtures thereof. A currently most preferred phospholipid is Lipoid E80.

The conglomerate preferably comprises from 1 to 70 weight percent of the substrate to be milled. The ratio of carrier fluid to substrate to be milled preferably ranges from less than 0.01 to 10, more preferably from 0.1 to 1. Substrates to be milled are generally solid at milling temperatures and preferably crystalline.

The concentration of surface active substance that can be added to the substrate to be milled or formulations of substrate to be milled according to this invention can range from 0.1 to 50 weight %, preferably 0.2 to 20 weight %, and more preferably 0.5 to 10% weight percent. The surface active agent stabilizes the very small milled substrate particles formed in the milling process of this invention. The surface active agent can be present as a single surface active substance or as a mixture of two or more surface active substances.

The total concentration of one or of more than one surface active substance (or surface active agent) added to a formulation prepared according to this invention can be in the range of 0.1 to 50 weight %, preferably 0.2 to 20 weight %, and more preferably 0.5 to 10 weight %.

By very small particles containing a poorly water-soluble drug is meant particles in the range of 0.05 micrometer to 20 micrometers in average diameter containing a poorly water-soluble drug, preferably in the range of 0.05 to 5 micrometers containing a poorly water-soluble drug, and most preferably in the range of 0.05 to 2 micrometer containing a poorly water-soluble drug.

As used herein, the term "poorly water-soluble" include "water-insoluble" and "essentially water-insoluble" in meaning.

In a preferred aspect, the present invention provides a process for the preparation of a dispersion comprising very small particles of a poorly water-soluble pharmaceutical to compound in a fluid carrier optionally in the presence of a surface active substance consisting of the steps of:

(a) providing a plurality of large size milling media to the milling chamber of a media mill and forming a depth filter therefrom on an exit screen or separator in the milling chamber;

(b) adding to said milling chamber a plurality of small size milling media optionally containing additional large size milling media, a conglomerate of a solid substance comprising a poorly water-soluble pharmaceutical compound to be milled and optionally one or more than one surface active substance, and a fluid carrier;

(c) milling said conglomerate in said milling chamber to produce very small milled substrate product particles comprising the poorly water-soluble pharmaceutical compound; and (d) removing or separating said milled substrate particles suspended in said fluid carrier from the media through said depth filter; wherein:
the exit screen comprises openings of size $S_0$;
the large size media have a size distribution $S_1$ of which all are larger than $S_0$;
the small size media have a size distribution $S_2$ which are smaller than $S_0$;
the very small milled substrate particles comprising the poorly water-soluble pharmaceutical compound have a size distribution $S_3$ and are smaller than all of the small media; and
the large size media and the small size media are retained in the milling chamber.

Small media can range in size from about 0.030 to 3 mm. For fine grinding, the small media particles preferably are from 0.03 to 0.5 mm, more preferably, 0.03 to 0.3 mm in size.

In another preferred aspect, the present invention provides a process for the preparation of a dispersion comprising very small particles of a poorly water-soluble pharmaceutical compound in a fluid carrier optionally in the presence of a surface active substance consisting of the steps of:

(a) providing a plurality of large size milling media to the milling chamber of a media mill and forming a depth filter therefrom on an exit screen or separator in the milling chamber;

(b) adding to said milling chamber a plurality of small size milling media optionally containing additional large size milling media, a conglomerate of a solid substance comprising a poorly water-soluble pharmaceutical compound to be milled and optionally one or more than one surface active substance, and a fluid carrier;

(c) milling said conglomerate in said milling chamber to produce very small milled substrate product particles comprising the poorly water-soluble pharmaceutical compound; and (d) continuously removing or separating said very small milled substrate particles suspended in said fluid carrier from the milling media through said depth filter; wherein:

the exit screen comprises openings of size $S_0$;

the large size media have a size distribution $S_1$ of which all are larger than $S_1$;

the small size media have a size distribution $S_2$ which are smaller than $S_0$;

the very small milled substrate particles comprising the poorly water-soluble pharmaceutical compound have a size distribution $S_3$ and are smaller than all of the small media; and the large size media and the small size media are retained in the milling chamber.

In the process of this invention, the volume of large milling media can comprise from 1% to 95% of the total milling media volume and the volume of small milling media can comprise from 99% to 5% of the total milling media volume in the milling chamber. More preferably, the volume of large milling media can comprise from 10% to 85% of the total milling media volume and the volume of small milling media can comprise from 90% to 15% of the total milling media volume in the milling chamber. Even more preferably, the volume of large milling media can comprise from 35% to 70% of the total milling media volume and the volume of small milling media can comprise from 65% to 30% of the total milling media volume in the milling chamber. Essential to the process of this invention is that there be sufficient numbers of large size milling media present to form a depth filter on the exit screen or exit separator of the media mill. The depth filter can consist of large size milling media as well as small sized milling media.

The invention is further illustrated by reference to the following non-limiting examples.

EXAMPLES

Example 1

In the milling chamber of a Netzsch Labstar LS1 media mill purged with nitrogen and having a pump for recirculating flow and an exit screen with opening sizes of 100 microns is placed 240 grams of 300 micron diameter zirconium silicate (Torayceram) beads and sufficient pH 8.0 aqueous phosphate buffer to cover the beads. The agitator is started and the large size beads are allowed to form a depth filter on the exit screen. The mill is then charged with 240 grams of 200 to 400 mesh (75 to 38 microns) styrene-divinylbenzene crosslinked beads and a conglomerate comprising 10% w/v fenofibrate (Sigma Chemical) and 3% w/v of the phospholipid Lipoid E80 (Avanti Polar Lipids, Inc.) and aqueous phosphate buffer adjusted to pH 8.0. The mill and pump are operated to initiate the milling process and flow of phosphate buffer fluid carrier. The size distribution of the product particles in the fluid carrier in the holding tank is smaller than the small sized beads. No styrenic milling media are found in the product dispersion suspended in the fluid carrier.

Example 2

A Draiswerke Perl Mill PML-H/V was configured for the formation of a depth filter to retain small milling media in the milling vessel. The media mill had a volume of about 0.75 liters, and a standard polyurethane perforated disc agitator with four discs. The end disc of the agitator was controlled to be proximal to the exit screen such that it could disrupt the depth filter during very high energy milling conditions when desired. The vessel was operated in a vertical position with the screen and exit port on the bottom to facilitate the formation of the depth filter. The exit screen in the milling chamber was composed of stacked ceramic spacers with a gap determined by the size of a washer placed between the spacers. In this example, the gap was set to 0.6 mm. The number of gaps could be varied, and in this example the number was set to 10 gaps. The inlet flow of dispersion was configured to be at the top of the vessel. The vessel was configured to operate in a continuous mode with the outlet flow from the vessel going by piping to a stirred tank having a total volume of about 5 liters. The tank was cooled by a water jacket to which was supplied cooling water chilled to about 11° C. A peristaltic pump located at the outlet port of the stirred tank could pump the fluid carrier and subsequently produced very small substrate particle containing dispersion back to the top of the milling vessel, thence through the milling vessel, through the depth filter, and back to the stirred tank. The milling vessel was charged with 900 grams of ZrO as a plurality of large milling media (0.9–1.1 mm) and 900 grams of small ZrO milling media (0.3–0.4 mm); water (2800 ml) was placed in the stirred tank. The pump was started at about 30 kg/hr to pump the water into the milling vessel. When the water came out of the milling vessel, the agitator in the milling vessel was started at 2830 rpm. Initially, some of the small media particles were observed to be pumped from the milling vessel into the stirred tank. After about three minutes, the small media particles stopped coming from the milling vessel indicating that the depth filter had formed on the screen and was restricting the flow of small media particles from the milling vessel.

Example 3

The procedure of Example 2 was repeated using a screen with 20 gaps each of 0.4 mm. The large milling media consisted of 834 grams of ZrO with a particle size nearly uniform at 0.65 mm. The small milling media consisted of 280 grams of polystyrene beads with a diameter of 0.15–0.25 mm. The pump and agitator were started with the pump operated at about 20 kg/hr. When the flow of water was started, some small milling media particles initially emerged from the milling chamber of the media mill vessel but after about two to three minutes the number of small particles leaving the milling vessel was essentially zero indicating the depth filter was restricting the flow of small particles from the milling vessel.

Example 4

Example 3 was repeated except that only small milling media beads (410 grams) were placed in the milling chamber of the media milling vessel. When the pump and agitator were started, the small milling media were carried out of the milling vessel with the recirculating water. When the pump and agitator were stopped, the concentration of small size milling media in the stirred tank was measured to be about 27 volume %. This was consistent with a mass balance calculation which gave a similar concentration for the small media as if distributed throughout the entire volume of water. Thus, there was no restriction of the flow of small milling media from the milling vessel in the absence of large size milling media and a depth filter formed therefrom, and no restriction of milling media flow was being caused by the screen.

Example 5

The method of Example 2 was repeated using a screen having 10 gaps of 0.6 mm, 900 grams of ZrO large media (0.9–1.1 mm) and 900 grams of ZrO small media (0.3–0.4 mm). The stirred tank was filled with 2800 ml of liquid-containing conglomerate which had the following composition, by weight: 2.0 parts deionized water as a fluid carrier, 0.260 parts fenofibrate as a poorly water-soluble drug, 0.078 parts Lipoid E-80 as a surface active agent, and 0.260 parts sucrose as a carbohydrate excipient. The initial dispersion of the conglomerate in water had a volume mean particle size of about 10 micrometers. The pump was operated at 30 kg/hr. Initially, there were some small media in the outlet of the milling vessel until the depth filter formed. After about 5 minutes, the flow out of the milling vessel contained essentially no small media indicating that the depth filter on the screen in the milling vessel was restricting the flow of small media out of the vessel. The mill and pump were operated until the volume weighted mean particle size of the recirculating dispersion of very small particles of fenofibrate stabilized with Lipoid E-80 produced in the process was 0.84 micrometers.

Example 6

A media mill configured as in example 5 was charged with 834 grams of ZrO (0.65 mm diameter) as large size milling media and 280 grams of polystyrene (0.15–0.25 mm) as small sized media. The screen was configured with 20 gaps of 0.4 mm, and the pump feed rate was set to about 20 kg/hr. The stirred water tank was charged with 2 kg of water, and the mill and pump were started as in example 2. As the water was pumped through the milling vessel, the following components of a conglomerate were added in succession in the ratios used in example 5: sucrose, then Lipoid E-80, and then fenofibrate. After about 5 minutes of pumping the water through the exit screen in the media mill, essentially all of the small milling media was restricted from leaving the milling vessel by the depth filter that was established on the exit screen. Milling was continued until the particle size distribution of the recirculating dispersion of very small particles of fenofibrate stabilized with Lipoid E80 produced in the process had a volume weighted mean particle size of 0.73 micrometers.

Example 7

Example 6 was repeated using a screen with 10 gaps of 0.3 mm, 1010 grams of ZrO with a size of 0.4–0.6 mm as the large size milling media, and 216 grams of polystyrene beads with a size of 0.15–0.25 mm as the small milling media. The pump flow rate was 30 kg/hr. The stirred tank was charged with 2 kg of water, and components of the conglomerate were added in the same amounts and the same way as in Example 6. Initially, small sized milling media particles flowed out of the milling vessel until a depth filter was established, whereupon the amount of small milling particles leaving the milling vessel substantially decreased as the depth filter restricted the flow of small milling media leaving the milling vessel. However, at the rate of agitation used for this entire milling experiment a small amount of small milling media continued to flow from the milling vessel indicating that the depth filter was being repeatedly disrupted by the disk agitator proximal to it in the milling chamber. Milling was continued until the volume weighted mean diameter of the very small particles of fenofibrate in the recirculating dispersion was 0.84 micrometers. The dispersion of very small particles of fenofibrate stabilized by Lipoid E-80 was separated by filtration from a small quantity of small sized milling media allowed through the disrupted depth filter.

Example 8

A Draiswerke Perl Mill PML-H/V with a milling chamber volume of about 0.75 liters and a standard polyurethane perforated disc agitator with four discs is configured for the formation of a depth filter to retain small sized milling media in the milling chamber. The end disc of the agitator is removed from proximity to the exit screen such that it does not disrupt the formation of a depth filter during milling conditions. The vessel is operated in a vertical position with the screen and exit port on the bottom to facilitate the formation of a depth filter. The exit screen in the milling chamber is composed of stacked ceramic spacers with a gap determined by the size of a washer placed between the spacers. Typically, the gap can be set to 0.6 mm as an example of an opening of size $S_0$. The number of gaps can be varied, and typically the number is set to 10 gaps. The inlet flow of the liquid fluid carrier and subsequent recirculating dispersion is configured to be at the top of the vessel. The vessel is configured to operate in a continuous mode with the outlet flow from the vessel going by a piping to a stirred tank having a total volume of about 5 liters. The outlet flow can be configured with valves and piping to flow directly back to inlet to the mill and by-passing the tank which can be charged with components of a conglomerate. The tank is cooled by a water jacket to which is supplied cooling water chilled to about 11° C. A peristaltic pump located at the outlet port of the stirred tank can pump the fluid carrier and any subsequently produced very small substrate particle-containing dispersion back to the top of the milling vessel, thence through the milling vessel, through the depth filter, and back to the stirred tank in continuous mode. To create the depth filter, the milling chamber of the media mill is charged with 900 grams of 0.9–1.1 mm ZrO as a plurality of large size milling media with a size distribution $S_1$ of which all are larger than $S_0$ as well as 900 grams of 0.3–0.4 mm ZrO as small sized milling media with a size distribution $S_2$ which is smaller than $S_0$. Water (2800 ml) is placed in the stirred tank, and the pump is started at about 30 kg/hr to pump the water into the milling vessel. When the water comes out of the milling vessel, the agitator in the milling vessel is started at 2830 rpm. Initially, the outflow is piped directly back to the inlet port of the media mill by-passing the holding tank. Some of the small media particles can be pumped from the milling vessel into the inlet port. After about five minutes, the small media particles stop coming from the milling vessel indicating that the depth filter is formed on the screen and is restricting the flow of small media particles from the milling vessel. The outflow of water free of small sized milling media is then diverted to the holding tank. The stirred holding tank is then charged with a conglomerate comprising the remaining volume of the 2800 ml representing 2.0 parts by weight of recirculating deionized water as the fluid carrier, 0.260 parts fenofibrate as a poorly water-soluble drug and milled substrate, 0.078 parts Lipoid E-80 as a surface active agent, and 0.260 parts sucrose as a carbohydrate pharmaceutical excipient. This conglomerate is pumped into the inlet port of the media mill and the mill and pump are run until the particle size of the very small particles recirculating in the mill through the depth filter into the tank is smaller than 1 micron, i.e., the very small milled substrate particles have a size distribution $S_3$ and are smaller than all of the small media. The large size media and the small size media are retained in the milling chamber, and the milled substrate particles suspended in the fluid carrier are continuously removed or separated from the milling media through the depth filter.

What is claimed is:

1. A process for preparing a dispersion of solid particles of a milled substrate in a fluid carrier comprising the steps of:
   (a) providing a plurality of large size milling media to the milling chamber of a media mill and forming a depth filter therefrom on an exit screen or separator in the milling chamber;
   (b) adding to said milling chamber a plurality of small size milling media optionally containing additional large size milling media, a conglomerate of a solid substance comprising a substrate to be milled and optionally one or more than one surface active substance, and a fluid carrier;
   (c) milling said conglomerate in said milling chamber to produce very small milled substrate product particles; and
   (d) continuously removing or separating said milled substrate particles suspended in said fluid carrier from the media through said depth filter; wherein:
   the exit screen or separator comprises openings of size $S_0$;
   the large size media have a size distribution $S_1$ of which all are larger than $S_0$;
   the small size media have a size distribution $S_2$ which are smaller than $S_0$;
   the very small milled substrate particles have a size distribution $S_3$ and are smaller than all of the small media; and
   the large size media and the small size media are retained in the milling chamber.

2. The process of claim 1, wherein the fluid carrier is a liquid.

3. The process of claim 1, wherein the fluid carrier is selected from the group consisting of water, sterile water, water for injection, aqueous solutions of one or more salts, solutions of aqueous buffers, aqueous phosphate buffered saline, sugar-containing water, aqueous solutions of one or more pharmaceutical excipients, aqueous solutions of one or more carbohydrates, aqueous solutions of one or more polymers, aqueous solutions of one or more than one surface active substance, aqueous solutions of one or more surface active substances mixed with one or more undissolved liquid surface active substances, PEG-containing water, ethanol, methanol, butanol, hexane, hydrocarbons, kerosene, glycol, toluene, glyme, petroleum-based solvents, ligroin, mixtures of aromatic solvents, xylenes, toluene, heptane, mixtures of water miscible solvents and water, DMSO, DMF, and mixtures of these fluid carriers.

4. The process of claim 1, wherein the fluid carrier is sterile.

5. The process of claim 1, wherein the surface active substance is selected from the group consisting of phospholipids, natural surfactants, nonionic surfactants, anionic surfactants, cationic surfactants, and colloidal clays.

6. The process of claim 5, wherein the surface active substance is a phospholipid or mixture of phospholipids.

7. The process of claim 6, wherein the phospholipid is selected from the group consisting of egg lecithin, egg phosphatidylcholine, hydrogenated egg phosphatidylcholine, soy phosphatidylcholine, dimyristoylphosphatidylglycerol, and combinations thereof.

8. The process of claim 1, wherein the solid substance is selected from the group consisting of a solid pigment, a solid photographic material, a solid cosmetic ingredient, a solid support material, a solid toner material, and a solid pharmaceutical agent.

9. The process of claim 8, wherein the pharmaceutical agent is a therapeutic agent or a diagnostic imaging agent.

10. The process of claim 8, wherein the pharmaceutical agent is a poorly water-soluble drug, an essentially water-insoluble drug, or an insoluble drug.

11. The process of claim 9, wherein the pharmaceutical agent is selected from the group consisting of anesthetic agents, ace inhibiting agents, antithrombotic agents, antiallergic agents, antibacterial agents, antibiotic agents, anticoagulant agents, anticancer agents, antidiabetic agents, antihypertension agents, antifungal agents, antihypotensive agents, antiinflammatory agents, antimitotic agents, antimigraine agents, antiparkinson agents, antirheumatic agents, antithrombins, antiviral agents, beta blocking agents, bronchospamolytic agents, calcium antagonists, cardiovascular agents, cardiac glycosidic agents, carotenoids, cephalosporins, contraceptive agents, cytostatic agents, diuretic agents, enkephalins, fibrinolytic agents, growth hormones, immunosuppressants, insulins, interferons, lactation inhibiting agents, lipid-lowering agents, lymphokines, neurologic agents, prostacyclins, prostaglandins, psychopharmaceutical agents, protease inhibitors, magnetic resonance diagnostic imaging agents, reproductive control hormones, sedative agents, sex hormones, somatostatins, steroid hormonal agents, vaccines, vasodilating agents, and vitamins.

12. The process of claim 8, wherein the pharmaceutical agent is selected from the group consisting of albendazole, albendazole sulfoxide, alfaxalone, acetyl digoxin, acyclovir, acyclovir analogs, aiprostadil, aminofostin, anipamil, antithrombin III, atenolol, azidothymidine, beclobrate, beclomethasone, belomycin, benzocaine, benzocaine derivatives, beta carotene, beta endorphin, beta interferon, bezafibrate, binovum, biperiden, bromazepam, bromocriptine, bucindolol, buflomedil, bupivacaine, busulfan, cadralazine, camptothesin, canthaxanthin, captopril, carbamazepine, carboprost, cefalexin, cefalotin, cefamandole, cefazedone, cefluoroxime, cefinenoxime, cefoperazone, cefotaxime, cefoxitin, cefsulodin, ceftizoxime, chlorambucil, chromoglycinic acid, ciclonicate, ciglitazone, clonidine, cortexolone, corticosterone, cortisol, cortisone, cyclophosphamide, cyclosporin A, cyclosporins, cytarabine, desocryptin, desogestrel, dexamethasone esters, dezocine, diazepam, diclofenac, dideoxyadenosine, dideoxyinosine, digitoxin, digoxin, dihydroergotamine, dihydroergotoxin, diltiazem, dopamine antagonists, doxorubicin, econazole, endralazine, enkephalin, enalapril, epoprostenol, estradiol, estramustine, etofibrate, etoposide, factor ix, factor viii, felbamate, fenbendazole, fenofibrate, flunarizin, flurbiprofen, 5-fluorouracil, flurazepam, fosfomycin, fosmidomycin, furosemide, gallopamil, gamma interferon, gentamicin, gepefrine, gliclazide, glipizide, griseofulvin, haptoglobulin, hepatitis B vaccine, hydralazine, hydrochiorothiazide, hydrocortisone, ibuprofen, ibuproxam, indinavir, indomethacin, iodinated aromatic x-ray contrast agents, iodamide, ipratropium bromide, ketoconazole, ketoprofen, ketotifen, ketotifen fumarate, K-strophanthin, labetalol, lactobacillus vaccine, lidoflazin, lisuride, lisuride hydrogen maleate, lorazepam, lovastatin, mefenamic acid, melphalan, memantin, mesulergin, metergoline, methotrexate, methyl digoxin, methylprednisolone, metronidazole, metisoprenol, metipranolol, metkephamide, metolazone, metoprolol, metoprolol tartrate, miconazole, miconazole nitrate, minoxidil, misonidazol, molsidomin, nadolol, nafiverine, nafazatrom, naproxen, natural insulins, nesapidil, nicardipine, nicorandil, nifedipine, niludipin, nimodipine, nitrazepam, nitrendipine, nitrocamptothesin, 9-nitrocamptothesin, oxazepam, oxprenolol, oxytetracycline, penicillins, penicillin G benethamine, penecillin O, phenylbutazone, picotamide, pindolol, piposulfan, piretanide, piribedil, piroxicam, pirprofen, plasminogenic activator, prednisolone, prednisone, pregnenolone, procarbacin, procaterol, progesterone, proinsulin, propafenone, propanolol, propentofyllin, propranolol, rifapentin, simvastatin, semi-synthetic insulins, sobrerol, somastotine, somatropin, stilamine, sulfinalol hydrochloride, sulfinpyrazone, suloctidil, suprofen, sulproston, synthetic insulin, talinolol, taxol, taxotere, testosterone, testosterone propionate, testosterone undecanoate, tetracane HI, tiaramide HCl, tolmetin, tranilast, triquilar, tromantadine HCl, urokinase, valium, verapamil, vidarabine, vidarabine phosphate sodium salt, vinblastine, vinburin, vincamine, vincristine, vindesine, vinpocetine, vitamin A, and vitamin E succinate.

13. The process of claim 8, wherein the pharmaceutical agent is selected from the group consisting of acyclovir, alprazolam, altretamine, amiloride, amiodarone, benztropine mesylate, bupropion, cabergoline, candesartan, cerivastatin, chlorpromazine, ciprofloxacin, cisapride, clarithromycin, clonidine, clopidogrel, cyclobenzaprine, cyproheptadine, delavirdine, desmopressin, diltiazem, dipyridamole, dolasetron, enalapril maleate, enalaprilat, famotidine, felodipine, furazolidone, glipizide, irbesartan, ketoconazole, lansoprazole, loratadine, loxapine, mebendazole, mercaptopurine, milrinone lactate, minocycline, mitoxantrone, nelfinavir mesylate, nimodipine, norfioxacin, olanzapine, omeprazole, penciclovir, pimozide, tacolimus, quazepam, raloxifene, rifabutin, rifampin, risperidone, rizatriptan, saquinavir, sertraline, sildenafil, acetyl-sulfisoxazole, temazepam, thiabendazole, thioguanine, trandolapril, triamterene, trimetrexate, troglitazone, trovafloxacin, verapamil, vinblastine sulfate, mycophenolate, atovaquone, atovaquone, proguanil, ceftazidime, cefuroxime, etoposide, terbinafine, thalidomide, fluconazole, amsacrine, dacarbazine, teniposide, and acetylsalicylate.

14. The process of claim 1, wherein the fluid carrier is selected from the group consisting of a gas, a liquefied compressed gas, a supercritical fluid, a supercritical fluid containing one or more dissolved excipients, and a supercritical fluid containing one or more surface active agents.

15. The process of claim 1, wherein the process comprises forming the depth filter on an exit screen comprising openings of less than 1 millimeter in size.

16. The process of claim 1, wherein the process comprises milling the conglomerate with large size media having a size that is at least 1.2 times larger than $S_0$.

17. The process of claim 16, wherein the process comprises milling the conglomerate with a large size media having a size that is at least 1.5 times larger than $S_0$.

18. The process of claim 17, wherein the process comprises milling the conglomerate with a large size media having a size that is at least 3 times larger than $S_0$.

19. The process of claim 1, wherein the process comprises milling the conglomerate with a small size media having a size that is smaller than $S_0$.

20. The process of claim 18, wherein the process comprises milling the conglomerate with a small size media having a size that is less than or equal to 0.95 times $S_0$.

21. The process of claim 20, where in the process comprises milling the conglomerate with a small size media having a size that is less than or equal to 0.85 times $S_0$.

22. The process of claim 1, wherein the process comprises milling the conglomerate in the milling chamber with a mixture of large milling media and small milling media, wherein the volume of large milling media makes up 1% to 95% of the total milling media volume in the milling chamber.

23. The process of claim 22, wherein the process comprises milling the conglomerate with a mixture of large and small milling media in which the volume of the large milling media makes up 10% to 85% of the total milling media volume in the milling chamber.

24. The process of claim 23, wherein the process comprises milling the conglomerate with a mixture of large and small milling media in which the volume of large milling media makes up 35% to 70% of the total milling media volume in the milling chamber.

25. The process of claim 1, wherein the process comprises producing and removing or separating milled substrate particles of less than 2 μm in size.

26. The process of claim 25, wherein the process comprises producing and removing or separating milled substrate particles of less than 1 μm in size.

27. The process of claim 26, wherein the process comprises producing and removing or separating milled substrate particles of less than 0.5 μm in size.

28. The process of claim 27, wherein the process comprises producing and removing or separating milled substrate particles of less than 0.4 μm in size.

29. The process of claim 28, wherein the process comprises producing and removing or separating milled substrate particles of less than 0.2 μm in size.

30. The process of claim 1, wherein the process comprises milling the conglomerate with large size milling media selected from the group consisting of spheres, cylinders, and toroids.

31. The process of claim 1, wherein the process comprises milling the conglomerate with small size milling media selected from the group consisting of polymeric beads, glass beads, zirconium silicate beads, and steel beads.

* * * * *